(12) United States Patent
Py

(10) Patent No.: US 10,351,271 B2
(45) Date of Patent: Jul. 16, 2019

(54) DEVICE FOR CONNECTING OR FILLING AND METHOD

(71) Applicant: Dr. Py Institute LLC, New Milford, CT (US)

(72) Inventor: Daniel Py, Larchmont, NY (US)

(73) Assignee: DR. PY INSTITUTE LLC, New Milford, CT (US)

( * ) Notice: Subject to any disclaimer, the term of this patent is extended or adjusted under 35 U.S.C. 154(b) by 0 days.

(21) Appl. No.: 14/536,566

(22) Filed: Nov. 7, 2014

(65) Prior Publication Data

US 2015/0122369 A1 May 7, 2015

Related U.S. Application Data

(63) Continuation-in-part of application No. 13/874,839, filed on May 1, 2013.

(Continued)

(51) Int. Cl.
*F16L 37/36* (2006.01)
*B65B 3/00* (2006.01)
(Continued)

(52) U.S. Cl.
CPC ............. *B65B 3/003* (2013.01); *A61M 39/26* (2013.01); *B65B 39/004* (2013.01); *A61M 39/18* (2013.01);
(Continued)

(58) Field of Classification Search
CPC ........ B65B 3/003; B65B 39/001; F16L 29/02; A61M 2039/268; A61M 39/26
(Continued)

(56) References Cited

U.S. PATENT DOCUMENTS 2,304,390 A * 12/1942 Wolfram ................. F16L 29/04
137/614.03
2,819,914 A 1/1958 Eitner
(Continued)

FOREIGN PATENT DOCUMENTS

EP 0174011 3/1986
EP 2042798 A1 4/2009
(Continued)

OTHER PUBLICATIONS

International Search Report and Written Opinion of the International Searching Authority for International Application No. PCT/US2013/039059, dated Aug. 22, 2013.

*Primary Examiner* — Umashankar Venkatesan
(74) *Attorney, Agent, or Firm* — McCarter & English, LLP

(57) ABSTRACT

A valve comprises a shell, a flexible valve member sealingly mounted within the shell, and a valve body mounted atop the flexible valve member within the shell. The flexible member is moveable between closed and open positions to allow the flow of fluid therethrough. The valve is engageable with a filling device having flow ports and a surrounding closure. The closure and/or the shaft is movable between (i) a first position wherein the closure closes the port(s), and (ii) a second position opening the port(s). Alternatively, the valve may comprise a portion of a female connector and the filling device may comprise a portion of a male connector to form an aseptic fluid connector for the aseptic transfer of fluid therethrough.

51 Claims, 16 Drawing Sheets

Related U.S. Application Data

(60) Provisional application No. 61/641,628, filed on May 1, 2012, provisional application No. 61/794,255, filed on Mar. 15, 2013.

(51) Int. Cl.
  *B65B 39/00* (2006.01)
  *A61M 39/26* (2006.01)
  *A61M 39/18* (2006.01)
  *B65B 55/02* (2006.01)

(52) U.S. Cl.
  CPC ...... *A61M 2039/268* (2013.01); *B65B 55/027* (2013.01)

(58) Field of Classification Search
  USPC ............ 137/614.04, 614.05, 614.06, 614.11, 137/616.3, 614.02, 614
  See application file for complete search history.

(56) References Cited

U.S. PATENT DOCUMENTS

| | | |
|---|---|---|
| 3,367,366 A | 2/1968 | Oliveau et al. |
| 3,692,029 A | 9/1972 | Adair |
| 3,750,667 A | 8/1973 | Pshenichny et al. |
| 3,777,771 A | 12/1973 | De Visscher |
| 3,848,645 A | 11/1974 | Franz |
| 4,052,989 A | 10/1977 | Kline |
| 4,413,985 A | 11/1983 | Wellner et al. |
| 4,421,146 A | 12/1983 | Bond et al. |
| 4,610,469 A | 9/1986 | Wolff-Mooij |
| 4,700,744 A | 10/1987 | Rutter et al. |
| 4,752,292 A | 6/1988 | Lopez et al. |
| 4,756,211 A | 7/1988 | Fellows |
| 4,778,447 A | 10/1988 | Velde et al. |
| 4,778,453 A | 10/1988 | Lopez |
| 4,790,832 A | 12/1988 | Lopez |
| 4,804,015 A | 2/1989 | Albinsson |
| 4,816,024 A | 3/1989 | Sitar et al. |
| 4,846,805 A | 7/1989 | Sitar |
| 4,894,055 A | 1/1990 | Sudnak |
| 4,917,149 A * | 4/1990 | Grantham ........... F16L 55/1015 137/614.03 |
| 4,931,048 A | 6/1990 | Lopez |
| 4,938,390 A | 7/1990 | Markva |
| 4,969,870 A | 11/1990 | Kramer et al. |
| 5,049,136 A | 9/1991 | Johnson |
| 5,104,382 A | 4/1992 | Brinkerhoff et al. |
| 5,122,123 A | 6/1992 | Vaillancourt |
| 5,176,643 A | 1/1993 | Kramer et al. |
| 5,199,947 A | 4/1993 | Lopez et al. |
| 5,211,197 A * | 5/1993 | Marrison ................ F16L 37/23 137/614 |
| 5,261,891 A | 11/1993 | Brinkerhoff et al. |
| 5,271,744 A | 12/1993 | Kramer et al. |
| 5,279,583 A | 1/1994 | Shober, Jr. et al. |
| 5,281,206 A | 1/1994 | Lopez |
| 5,312,364 A | 5/1994 | Jacobs |
| 5,344,414 A | 9/1994 | Lopez et al. |
| 5,380,306 A | 1/1995 | Brinon |
| 5,387,197 A | 2/1995 | Smith et al. |
| 5,429,256 A | 7/1995 | Kestenbaum |
| 5,451,210 A | 9/1995 | Kramer et al. |
| 5,478,328 A | 12/1995 | Silverman et al. |
| 5,482,083 A | 1/1996 | Jenski |
| 5,492,147 A | 2/1996 | Challender et al. |
| 5,520,666 A | 5/1996 | Choudhury et al. |
| 5,531,692 A | 7/1996 | Rogers |
| 5,549,577 A | 8/1996 | Siegel et al. |
| 5,575,804 A | 11/1996 | Yoon |
| 5,584,848 A | 12/1996 | Yoon |
| 5,607,439 A | 3/1997 | Yoon |
| 5,645,556 A | 7/1997 | Yoon |
| 5,669,891 A | 9/1997 | Vaillancourt |
| 5,685,852 A | 11/1997 | Turkel et al. |
| 5,694,686 A | 12/1997 | Lopez et al. |
| 5,713,874 A | 2/1998 | Ferber |
| 5,810,768 A | 9/1998 | Lopez |
| 5,810,792 A | 9/1998 | Fangrow, Jr. et al. |
| 6,032,691 A | 3/2000 | Powell et al. |
| 6,041,805 A * | 3/2000 | Gydesen ............. A61M 39/26 137/150 |
| 6,071,270 A | 6/2000 | Fowles et al. |
| 6,079,444 A | 6/2000 | Harris et al. |
| 6,113,068 A | 9/2000 | Ryan |
| 6,113,583 A | 9/2000 | Fowles et al. |
| 6,135,150 A | 10/2000 | Powell et al. |
| 6,135,167 A | 10/2000 | Kiholm |
| 6,183,442 B1 | 2/2001 | Athanasiou et al. |
| 6,245,048 B1 | 6/2001 | Fangrow, Jr. et al. |
| 6,299,131 B1 | 10/2001 | Ryan |
| 6,394,992 B1 | 5/2002 | Sjoholm |
| 6,409,304 B1 | 6/2002 | Taylor |
| 6,428,520 B1 | 8/2002 | Lopez et al. |
| 6,478,775 B1 | 11/2002 | Galt et al. |
| 6,497,686 B1 | 12/2002 | Adams et al. |
| 6,554,146 B1 | 4/2003 | DeGroff et al. |
| 6,599,273 B1 | 7/2003 | Lopez |
| 6,604,561 B2 | 8/2003 | Py |
| 6,685,674 B2 | 2/2004 | Douglas et al. |
| 6,695,817 B1 | 2/2004 | Fangrow, Jr. |
| 6,726,672 B1 | 4/2004 | Hanly et al. |
| 6,742,556 B1 | 6/2004 | Osuna et al. |
| 6,866,158 B1 | 3/2005 | Sommer et al. |
| 6,837,878 B2 | 6/2005 | Smutney et al. |
| 6,989,003 B2 | 1/2006 | Wing et al. |
| 6,994,315 B2 | 2/2006 | Ryan et al. |
| 7,077,176 B2 | 7/2006 | Py |
| 7,099,731 B2 | 8/2006 | Lopez |
| 7,100,646 B2 | 9/2006 | Py et al. |
| 7,156,826 B2 | 1/2007 | Ishii et al. |
| 7,174,914 B2 | 2/2007 | Ooishi et al. |
| 7,309,326 B2 | 12/2007 | Fangrow, Jr. |
| 7,354,427 B2 | 4/2008 | Fangrow |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,239 B1 | 5/2009 | Fangrow |
| 7,547,300 B2 | 6/2009 | Fangrow |
| 7,568,509 B2 | 8/2009 | Py |
| 7,569,043 B2 | 8/2009 | Fangrow |
| 7,645,271 B2 | 1/2010 | Fangrow |
| 7,648,491 B2 | 1/2010 | Rogers |
| 7,654,995 B2 | 2/2010 | Warren et al. |
| 7,658,733 B2 | 2/2010 | Fangrow |
| 7,670,322 B2 | 3/2010 | Fangrow, Jr. |
| 7,758,566 B2 | 7/2010 | Simpson et al. |
| 7,803,139 B2 | 9/2010 | Fangrow, Jr. |
| 7,824,393 B2 | 11/2010 | Fangrow |
| 7,883,499 B2 | 2/2011 | Fangrow |
| 7,892,216 B2 | 2/2011 | Fangrow, Jr. |
| 7,921,875 B2 | 4/2011 | Moriiki et al. |
| 7,931,615 B2 | 4/2011 | Fangrow, Jr. |
| 8,105,314 B2 | 1/2012 | Fangrow, Jr. |
| 8,196,606 B2 | 6/2012 | Kitagawa |
| 8,246,578 B2 | 8/2012 | Matsumoto |
| 8,348,881 B2 | 1/2013 | Aubert et al. |
| 8,409,164 B2 | 4/2013 | Fangrow |
| 8,454,579 B2 | 6/2013 | Fangrow, Jr. |
| 8,522,832 B2 | 9/2013 | Lopez et al. |
| 8,535,279 B2 | 9/2013 | Schweikert et al. |
| 8,552,832 B2 | 9/2013 | Lopez et al. |
| 8,647,310 B2 | 2/2014 | Fangrow, Jr. et al. |
| 8,696,625 B2 | 4/2014 | Carrel et al. |
| 8,758,306 B2 | 6/2014 | Lopez et al. |
| 8,759,306 B2 | 6/2014 | Lopez et al. |
| 8,808,200 B2 | 8/2014 | Miller et al. |
| 8,956,330 B2 | 2/2015 | Fangrow, Jr. |
| 2002/0032433 A1 | 3/2002 | Lopez |
| 2002/0120212 A1 | 8/2002 | Ritchart et al. |
| 2002/0188260 A1 | 12/2002 | Gollobin |
| 2002/0189712 A1 | 12/2002 | Safabash |

(56) References Cited

U.S. PATENT DOCUMENTS

| | | |
|---|---|---|
| 2003/0032940 A1 | 2/2003 | Doyle |
| 2003/0070726 A1 | 4/2003 | Andreasson et al. |
| 2003/0106610 A1 | 6/2003 | Roos et al. |
| 2003/0216667 A1 | 11/2003 | Viola |
| 2004/0124389 A1 | 7/2004 | Phillips |
| 2004/0222224 A1 | 11/2004 | Plester |
| 2004/0256026 A1 | 12/2004 | Py |
| 2006/0142735 A1 | 6/2006 | Whitley |
| 2006/0178646 A1 | 8/2006 | Harris et al. |
| 2006/0287639 A1 | 12/2006 | Sharp |
| 2007/0106225 A1 | 5/2007 | Millerd |
| 2007/0225635 A1 | 9/2007 | Lynn |
| 2008/0103487 A1 | 5/2008 | Miyasaka |
| 2008/0197626 A1 | 8/2008 | Coambs et al. |
| 2009/0082725 A1 | 3/2009 | Witowski |
| 2009/0091129 A1 | 4/2009 | Moriiki et al. |
| 2009/0243281 A1 | 10/2009 | Seifert et al. |
| 2009/0292274 A1 | 11/2009 | Guala |
| 2010/0021230 A1 * | 1/2010 | Olivier ............... A61M 39/10 403/11 |
| 2010/0108681 A1 | 5/2010 | Jepson et al. |
| 2010/0121305 A1 | 5/2010 | Rogers |
| 2010/0140290 A1 | 6/2010 | Py |
| 2011/0060312 A1 | 3/2011 | Scheurer |
| 2011/0106046 A1 | 5/2011 | Hiranuma et al. |
| 2011/0186764 A1 | 8/2011 | Takami |
| 2011/0240158 A1 | 10/2011 | Py |
| 2012/0042971 A1 | 2/2012 | Py |
| 2012/0118416 A1 | 5/2012 | Johnson |
| 2012/0220978 A1 | 8/2012 | Lev et al. |
| 2012/0261027 A1 | 10/2012 | Py |
| 2013/0046246 A1 | 2/2013 | Cross et al. |

FOREIGN PATENT DOCUMENTS

| | | |
|---|---|---|
| WO | 93/11828 | 6/1993 |
| WO | 9505863 | 3/1995 |
| WO | 0198158 A1 | 12/2001 |
| WO | 2009035383 | 3/2009 |
| WO | 2011146012 A1 | 11/2011 |

* cited by examiner

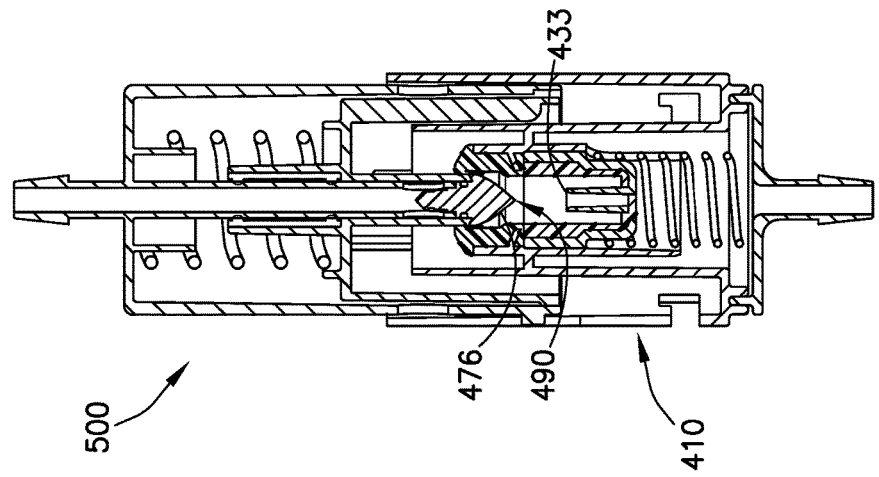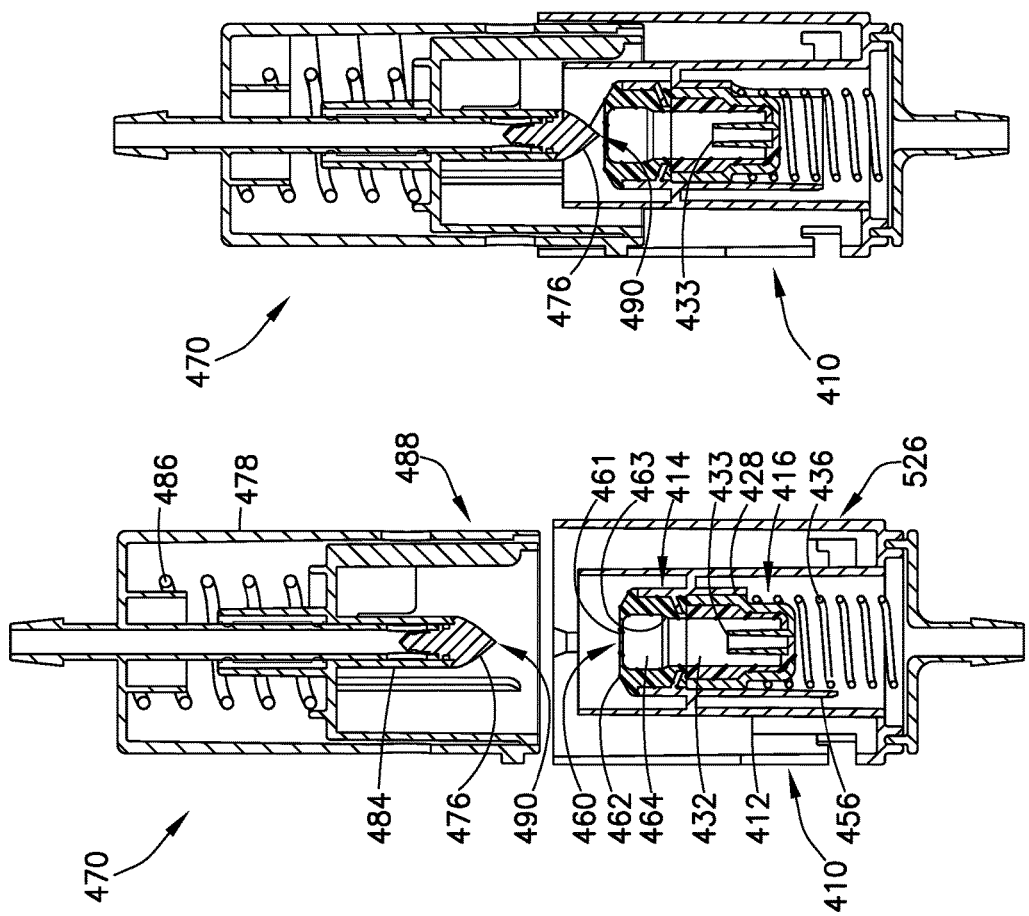

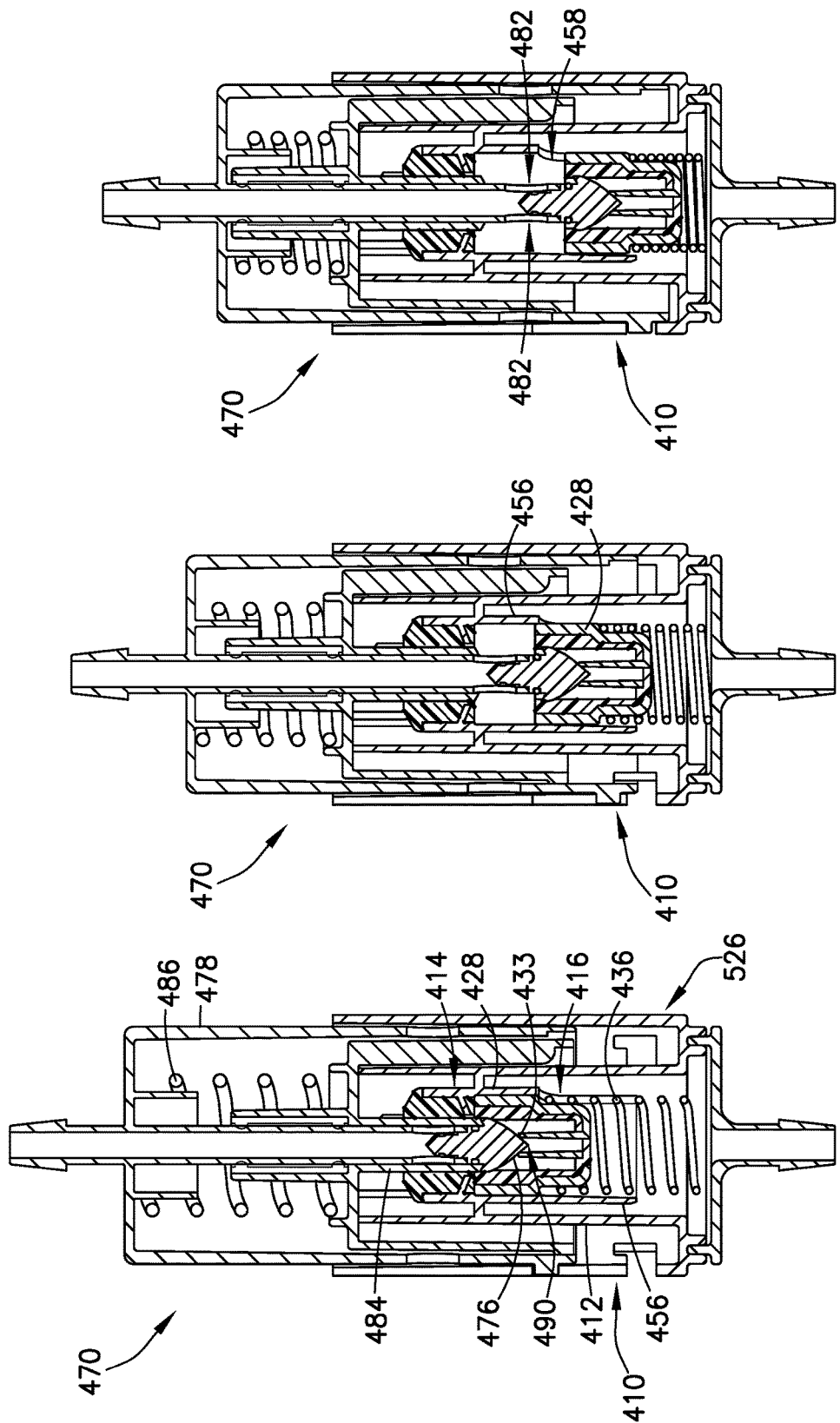

DEVICE FOR CONNECTING OR FILLING AND METHOD

CROSS-REFERENCE TO RELATED APPLICATIONS

This patent application is a continuation-in-part of U.S. patent application Ser. No. 13/874,839, filed May 1, 2013, which claims benefit under 35 U.S.C. § 119 to similarly-titled U.S. Provisional Patent Application Nos. 61/641,248, filed May 1, 2012, and 61/794,255, filed Mar. 15, 2013. All of the foregoing applications and patents are hereby expressly incorporated by reference as part of the present disclosure.

FIELD OF THE INVENTION

The present invention relates to filling devices and connectors, and methods of filling and transferring fluids, and more particularly to methods of aseptically filling devices and connectors for the aseptic filling and transfer of fluids.

BACKGROUND

A typical previously-known filling cannula or probe used for aseptic or so called "sterile" filling comprises a hollow filling tube including an outlet port in fluid communication between the hollow interior of the filling tube and ambient atmosphere. A previously-known filling cannula or probe, for example, includes a hollow stainless steel shaft, a bulbous tip fixedly secured to the distal end of the shaft, and diametrically opposed outlet ports proximal to the tip and in fluid communication between the interior of the shaft and the ambient atmosphere. One drawback encountered with previously-known filling cannulas and needles is that the interior of the cannula or probe, and any fluid contained therein or passing therethrough, can be exposed to the ambient atmosphere via the open fluid ports. In connection with known filling machines, regulatory agencies require control of the cannula or probe environment in order to protect against exposure of a sterile product to the environment and the resulting contamination of the product that might occur. However, typical controlled environments, such as a class 100 (ISO-5) controlled environment, are not truly sterile. Although the likelihood of contamination in such reduced-contaminant environments may be relatively low, just one colony of contaminants can develop into a container full of germs over its shelf-life. This risk is exacerbated when filling traditional open containers that are thereafter sealed in an assembly machine. No such previously-known assembly machine, such as, for example, a typical machine closing 40,000 containers per hour, can fully prevent entrance of viables and non-viables into the containers. On the other hand, if the cannula or probe is used to dispense a contaminated fluid, or a fluid that might be harmful if it is exposed to or comes into contact with an operator, the open ports can allow such fluid to contaminate its ambient atmosphere or potentially harm the operator that contacts the cannula or probe or is in the vicinity thereof.

A typical fluid connector includes a male connector that is received within a female connector to place the two connectors in fluid communication with each other. The male and female connectors may be threadedly engaged, snap fit, or otherwise releasably connected to each other to allow for interconnection and disconnection. Each connector is coupled in fluid communication with a respective fluid passageway, such as a tube or fluid chamber, in order to place the fluid passageways in fluid communication with each other and allow the passage of fluids through the connected elements.

Such fluid connectors typically do not prevent the contamination of fluids passing through them, unless the connector is sterile handled and connected in a relatively low challenging environment (even then, the connectors must be sealingly connected to each other to prevent ingress of contaminants, which means the connection cannot be disengaged). For example, prior to interconnection of the male and female connectors, the fluid-contacting surfaces thereof can be exposed to the ambient atmosphere and contaminated through contact with airborne germs and/or by contact with contaminated surfaces. One approach to preventing such contamination is to wipe the fluid-contacting surfaces of the male and female connectors with an alcohol wipe or other disinfectant prior to interconnection. One drawback of this approach is that the fluid-contacting surfaces may become contaminated after the wipe is applied to the male and female connectors. Another drawback of this approach is that it can be time consuming and considered a nuisance, and therefore unreliable in practice. There is no previously-known connector capable connection within a contaminated liquid or contaminated aerosol chamber that prevents the contamination of fluids passing therethrough.

Accordingly, aseptic or sterile fluids can be subjected to contamination when passed through such previously-known connectors. If used in a hospital or other medical facility, such as to transfer sterile drugs or other fluids intended for intravenous injection, for example, any such contamination can lead to bloodstream infections, e.g., catheter related blood stream infections (CRBSI). CRBSI represent about 15% of nosocomial infections per year. According to the Center for Disease Control (CDC), approximately 200,000 cases CRBSI are reported in the United States per year and cost the country about $35 billion in treatment costs. CRBSI leads to about 30,000 deaths per year in United States hospitals. In food processing applications, on the other hand, it may be necessary to connect fluid conduits, for example, in order to transfer sterile or aseptic fluids from one passageway to another. If the fluids are contaminated upon passage through a fluid connector, this can lead to contamination of previously-sterile food products, and if such contaminated products are ingested, they can cause infections and/or illnesses. In industrial applications, it may be necessary to prevent a toxic fluid passing through a connector from contaminating the ambient atmosphere, an operator handling the connector, and/or other surfaces that might be located external to the connector. If the fluid-contacting surfaces of the connector are exposed to human contact, or surfaces that come into human contact, for example, this can lead to possible injury and/or illnesses. For example, operators exposed to the transfer of liquids such as immune suppressants or hormones, can suffer from pulmonary absorption of such products.

SUMMARY OF THE INVENTION

It is an object of the present invention to overcome one or more of the above-described drawbacks and/or disadvantages of the prior art, including to reduce the risk of contamination of a fluid during transfer and/or filling thereof, and mitigating illness and death from nosocomial infections.

In accordance with a first aspect, a device comprises a tube including a flow inlet, a flow outlet in fluid communication with the flow inlet, and a closure; wherein at least one of the closure and the tube is movable between (i) a first position where the closure closes the flow outlet, and (ii) a second position where the flow outlet is open. To prevent contamination, the closure forms a substantially fluid-tight seal between the flow outlet and ambient atmosphere.

In some embodiments, the closure is biased in a direction from the second position toward the first position to normally close the flow outlet. In some such embodiments, the device includes a spring biasing the closure in the direction from the second position toward the first position.

In some embodiments, the tube is connectable to a device for filling, having a valve connected to a chamber thereof, where in the second position, the flow outlet is connectable in fluid communication with the chamber through the valve to fill substance from the flow inlet, through the flow outlet and valve, and into the chamber. In some such embodiments the device for filling includes a septum overlying the valve, and the closure is engageable with the septum to allow movement of at least one of the tube and closure relative to the other from the first position to the second position during or after movement of the tube through the septum. In some such embodiments, the valve includes a recess, the tube includes a tip that is receivable within the recess, and the closure is engageable with the device to be filled to allow movement of at least one of the tube and closure relative to the other from the first position to the second position during or after movement of the tube tip into the recess. In some such embodiments, the valve includes a spring that normally biases the valve in the direction from the open position to the closed position. In some such embodiments, the valve spring is approximately dome shaped.

In accordance with another aspect, a device comprises first means for the flow of substance to be filled therethrough; second means in fluid communication with the first means for the passage of the substance from the first means therethrough; and third means for opening and closing the third means, wherein at least one of the first means and the third means is movable between (i) a first position where the third means closes the second means, and (ii) a second position where the second means is open.

In some embodiments, the first means is a tube, the second means is a flow outlet of the tube, and the third means is a closure.

In some embodiments, the device further comprises fourth means for biasing the third means in a direction from the second position toward the first position to normally close the second means.

In accordance with another aspect, a method comprises the following steps:
(i) introducing an aseptic or sterile substance into a cannula;
(ii) sealing an outlet of the cannula with respect to ambient atmosphere and preventing the flow of aseptic or sterile substance in the cannula from flowing through the outlet; and
(iii) opening the outlet of the cannula and introducing the aseptic or sterile substance from the cannula through the outlet and into a storage chamber of a device to be filled.

In some embodiments the cannula further includes a tube defining an inlet and the outlet, and a closure, wherein the step of opening further comprises moving at least one of the closure and the tube between (i) a first position, where the closure closes the outlet, and (ii) a second position wherein the outlet is open. In some such embodiments, the method further comprises sealing the outlet from ambient atmosphere in the first position. In some such embodiments the method further comprises passing the cannula through a septum coupled to a valve in fluid communication with the storage chamber, engaging the valve, and introducing the aseptic or sterile substance from the outlet of the cannula through the valve. In some such embodiments, the engaging step further comprises opening the valve to allow the introduction of substance through the valve and into the storage chamber. In some such embodiments, the step of opening the valve comprises moving a flexible valve member of the valve from a sealingly closed position to an open position.

In some embodiments, the method further comprises disengaging the cannula from the valve; and before or during the disengaging step, moving at least one of the closure and the tube from the second position to the first position, and simultaneously moving the valve from the open position to the sealing closed position.

In some embodiments, contact is substantially prevented between the outlet of the cannula and the septum during the engaging and disengaging steps. In some such embodiments, the closure is interposed between the outlet of the cannula and the septum to substantially prevent any contact between the outlet and the septum.

In some embodiments, the method further comprises engaging, introducing and disengaging steps in a non-sterile environment or an environment defining a SAL of about 6 log bio-burden on the surface or less; introducing a sterile fluid through the cannula and into the storage chamber; and maintaining the sterility of the filled fluid throughout the engaging, introducing and disengaging steps.

In accordance with another aspect, a connector comprises a first connector portion including a filling member comprising a hollow shaft, a tip formed at one end of the shaft, at least one port in fluid communication with an interior of the hollow shaft, and a closure; wherein at least one of the closure and the shaft is movable between (i) a first position wherein the closure closes the at least one port, and (ii) a second position opening the at least one port. The connector further includes a second connector portion adapted to engage the first connector portion and including a valve, which can have a flexible valve member and a valve seat configured to be moved between (i) a closed position, wherein the flexible valve member is sealingly engaged by the valve seat, thereby preventing the flow of fluid therethrough, and (ii) an open position, wherein the flexible valve member is disengaged from the valve seat to allow the flow of fluid therethrough; wherein at least one of the first connector portion and the second connector portion is moveable relative to each other between (i) a disconnected position wherein at least one of the closure and the shaft is in the first position and the valve is in the closed position, and (ii) a connected position wherein the filling member has engaged and moved the valve from the closed position to the open position, and the at least one of the closure and the shaft is in the second position opening the at least one port.

In some embodiments, the closure forms a substantially fluid-tight seal between the at least one port and the ambient atmosphere in the first position.

In some embodiments, the closure is normally biased in the direction from the second position toward the first position to normally close the at least one port.

In some embodiments, the flexible valve member is normally biased in the direction from the open position toward the closed position, to normally sealingly close the valve from the passage of fluid therethrough.

In some embodiments, the first connector portion further includes a biasing member that normally biases the closure in the direction from the second position to the first position. In some such embodiments, the biasing member includes a sealing member for sealing engaging the hollow shaft of the filling member. In some such embodiments, the sealing member is integrally formed with the biasing member. In some such embodiments, the sealing member comprises an O-ring. In some embodiments, the biasing member is an approximately dome-shaped elastic spring.

In some embodiments, the flexible valve member comprises an integral spring that normally biases the flexible valve member in the direction from the open position toward the closed position, to normally sealingly close the valve from the passage of fluid therethrough. In some such embodiments, the integral spring is an elastic approximately dome-shaped spring.

In some embodiments, the first connector portion further includes a one-way valve. In some such embodiments, the one-way valve is configured to vent out air from a chamber defined by a dome-shaped spring biasing member to the ambient atmosphere, when at least one of the closure and the shaft is moved from the first position to the second position. In some such embodiments, the one-way valve is configured to vent in air from the ambient atmosphere into the chamber defined by the dome shaped spring biasing member, when at least one of the closure and the shaft is moved from the second position to the first position. In some such embodiments, the one-way valve is integrally formed with the approximately dome shaped spring biasing member.

In some embodiments, the second connector portion further comprises a septum overlying the flexible valve member of the valve. In some such embodiments, the septum defines a durometer within the range of about 5 Shore A to about 65 Shore A. In some such embodiments, the septum defines a durometer within the range of about 25 Shore A to about 45 Shore A. In some such embodiments, the septum defines a thickness within the range of a thickness equivalent to about ½ the diameter of the filling member to a thickness equivalent to about double the diameter of the filling member.

In some embodiments, the closure is engageable with the septum of the second connector portion to prevent further movement of the closure relative to the second connector portion, whereby subsequent movement of the first connector portion moves the shaft from the first position to the second position.

In some embodiments, movement of one of the first connector portion and the second connector portion relative to the other of the first connector portion and the second connector portion from the disconnected position to the connected position achieves at least approximately a 3 log reduction in bio-burden.

In some embodiments, at least one of the closure and the shaft is movable from the second position to the first position, and the valve is movable from the open position to the closed position during or upon disengaging the filling member from the valve.

In some embodiments, the closure includes a shutter extending annularly about the shaft.

In accordance with another aspect, a connector comprises: first means for providing fluid to a second means for engaging the first means and for receiving fluid from the first means; the first means comprising third means for providing a conduit for the passage of fluid therethrough; fourth means formed at one end of the third means for engaging a valve; fifth means in fluid communication with the third means for passage of fluid from the third means therethrough; and sixth means for closing the third means; wherein at least one of the third means and the sixth means is movable between (i) a first position wherein the sixth means closes the fifth means; and (ii) a second position opening the fifth means; the second means comprising seventh means for engaging by the third means when the first means and the second means are in a connected position with each other; wherein a the seventh means is moveable between (i) a closed position, wherein the seventh means prevents the flow of fluid therethrough; and (ii) an open position, wherein the seventh means allows the flow of fluid therethrough; wherein at least one of the first means and the second means is moveable relative to each other between (i) a disconnected position wherein the at least one of the third means and the sixth means is in the first position and the seventh means is in the closed position; and (ii) a connected position wherein the fifth means has engaged and moved the seventh means from the closed position to the open position and the at least one of the third means and the sixth means is in the second position opening the fifth means.

In some embodiments, the first means is a first connector portion, the second means is a second connector portion, the third means is a filling member, the fourth means is a tip of the filling member, the fifth means is at least one port, the sixth means is a closure, and the seventh means is a valve.

In accordance with another aspect, a method comprises the following steps:

(i) engaging a first connector portion with a second connector portion, the first connector portion including a filling member comprising a hollow shaft, a tip formed at one end of the shaft, at least one port in fluid communication with an interior of the hollow shaft, and a closure; wherein at least one of the closure and the shaft is movable between (i) a first position wherein the closure closes the at least one port, and (ii) a second position opening the at least one port; wherein the second connector portion is adapted to engage the first connector portion and including a valve, having a flexible valve member and a valve seat, configured to be moved between (i) a closed position, wherein the flexible valve member is sealingly engaged by the valve seat, thereby preventing the flow of fluid therethrough, and (ii) an open position, wherein the flexible valve member is disengaged from the valve seat to allow the flow of fluid therethrough; and at least one of the first connector portion and the second connector portion is moveable relative to each other between (i) a disconnected position wherein the at least one of the closure and the shaft is in the first position and the valve is in the closed position, and (ii) a connected position wherein the filling member has engaged and moved the valve from the closed position to the open position, and the at least one of the closure and the shaft is in the second position opening the at least one port;

(ii) moving at least one of the first connector portion and second connector portion relative to each other from the disconnected position toward the connected position;

(iii) engaging the valve with the filling member (iv) moving the valve from the open position to the closed position;

(v) moving at least one of the closure and the shaft from the first position closing the at least one port to the second position opening the at least one port; and (vi) introducing fluid from the shaft through the at least one port and the valve.

In some embodiments, the step of moving at least one of the closure and the shaft from the first position to the second position occurs with the step of moving the valve from the open position to the closed position.

In some embodiments, the method further comprises the step of sterilizing the first connector portion and the second connector portion.

In some embodiments, the step of moving at least one of the first connector portion and the second connector portion relative to each other from the disconnected position toward the connected position comprises both axial and rotational movement.

In some embodiments, the second connector portion further comprises a septum overlying the valve and the step of moving at least one of the first connector portion and the second connector portion relative to each other from the disconnected position toward the connected position further comprises moving the filling member through the septum and wiping the filling member with the septum. In some such embodiments, the wiping step comprises wiping the tip of the filling member with the septum. In some such embodiments, the wiping step comprises wiping the filling member with a septum defining a durometer within the range of about 5 Shore A to about 65 Shore A. In some such embodiments, the wiping step comprises wiping the piercing member with a septum defining a durometer within the range of about 25 Shore A to about 45 Shore A. In some such embodiments, the wiping step comprises wiping the filling member with a septum defining a thickness within the range of a thickness equivalent to about ½ the diameter of the filling member to a thickness equivalent to about double the diameter of the filling member. In some such embodiments, the wiping step achieves at least approximately a 3 log reduction in bio-burden of the filling member.

In accordance with another aspect, the method further comprises the following steps:
(vii) disengaging the filling member from the valve;
(viii) before or during the disengaging step, moving at least one of the closure and the shaft from the second position to the first position, and moving the valve from the open position to the closed position;
(ix) moving the at least one of the first connector portion and the second connector portion relative to each other from the connected position to the disconnected position; and
(x) separating the first connector portion and the second connector portion.

In some embodiments, contact between the at least one filling port and the septum is substantially prevented during the engaging and disengaging steps.

In some embodiments, the method further comprises performing the engaging, introducing and disengaging steps in a non-sterile environment or an environment defining a SAL of about log 3 or less; introducing a sterile fluid through the first and second connector portions; and maintaining the sterility of the filled fluid throughout the engaging, introducing and disengaging steps.

One advantage of the present invention is that it provides a closed system sterile transfer, such that product transferred within the system does not come in contact with the external environment or contaminants therefrom. Another advantage of the present invention is that the filling device and the connector can aseptically fill and transfer fluid within a non-aseptic, non-sterile or relatively low SAL environment (e.g., about log 6 or lower). Other objects and advantages of the present invention, and/or of the currently preferred embodiments thereof, will become more readily apparent in view of the following detailed description and the accompanying drawings.

BRIEF DESCRIPTION OF THE DRAWINGS

FIGS. 14A through 14F are sequential perspective views of another embodiment of male and female connectors, showing the male connector from alignment and engagement with the female connector, to full connection with the female connector, for transferring fluid therethrough.

DETAILED DESCRIPTION OF EMBODIMENTS OF THE INVENTION

Figure 1:
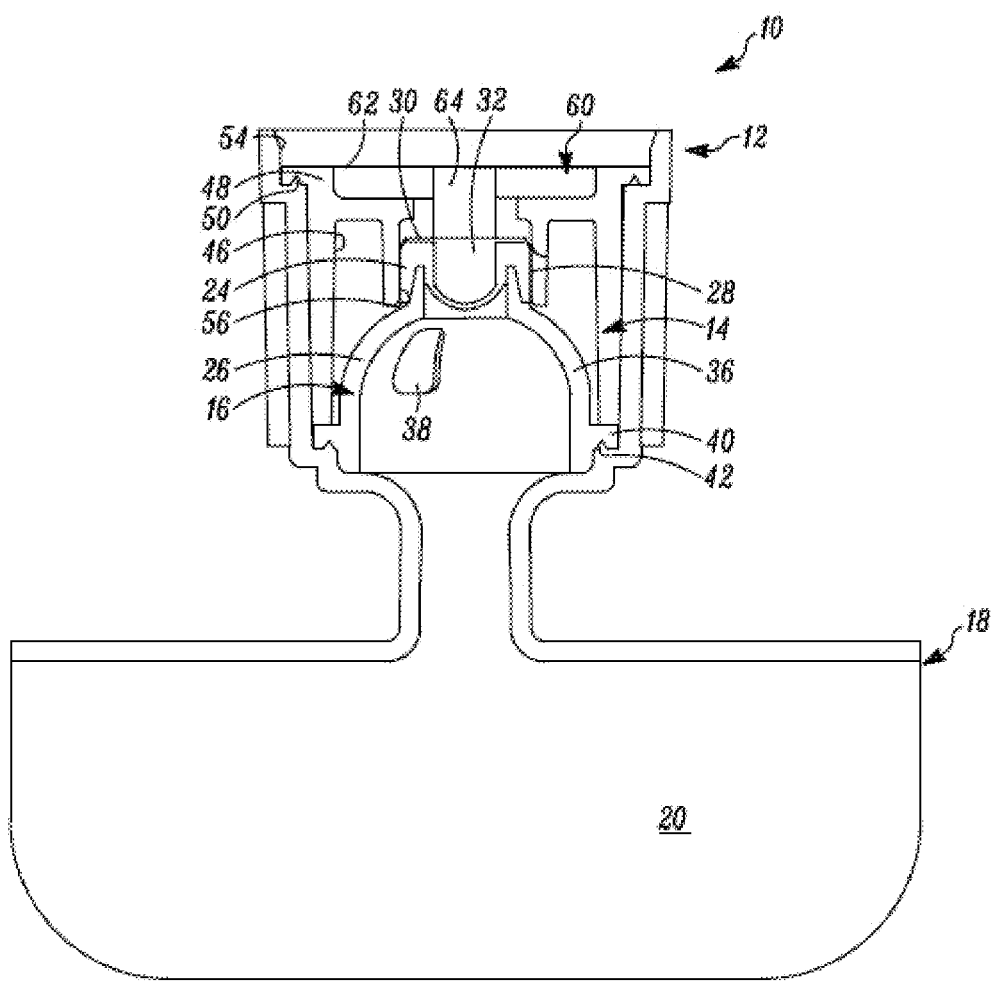
FIG. 1 is a cross-sectional view of a first embodiment of a valve coupled to a device having a chamber for filling and dispensing fluids or other substances therefrom.

In FIG. 1 a valve is indicated generally by the reference numeral 10. The valve 10 comprises a shell 12, a flexible valve member 16 sealingly mounted within the shell 12 and a valve body 14 mounted atop the flexible valve member 16 within the shell 12, as explained further below. In some embodiments, the shell 12 is made of a polymeric or thermoplastic material such as polypropylene (PP) or high-density polyethylene (HDPE). However, as may be recognized by those of ordinary skill in the pertinent art based on the teachings herein, the shell may be made of any of numerous different materials that are currently known or that later become known. The valve 10 is connected, at a bottom end thereof, in fluid communication with a container 18, defining a storage chamber 20 therein, via a neck 22. In the illustrated embodiment, the container 18 is a pouch. However, as may be recognized by those of ordinary skill in the pertinent art based on the teachings herein, the container may define any of numerous containers or devices defining storage chambers therein having any of numerous different configurations.

Figure 2:
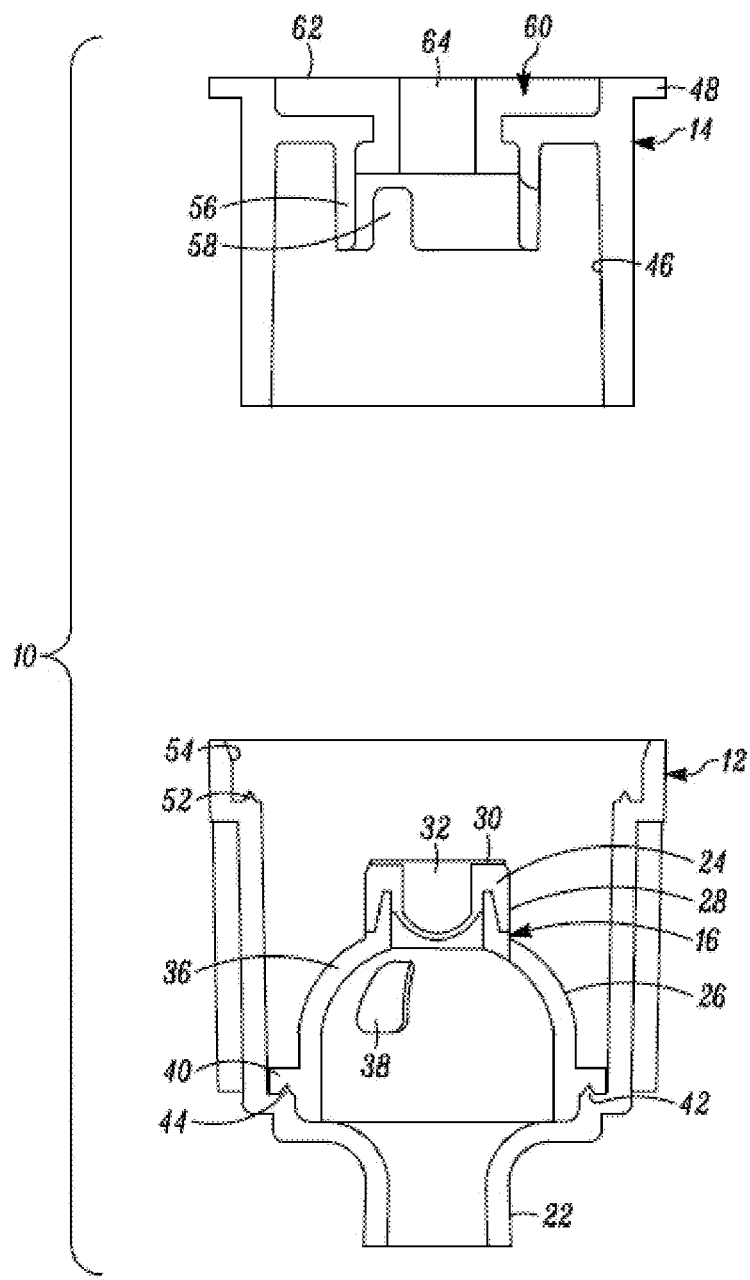
FIG. 2 is an exploded, cross-sectional view of the valve of FIG. 1.
Figure 3:
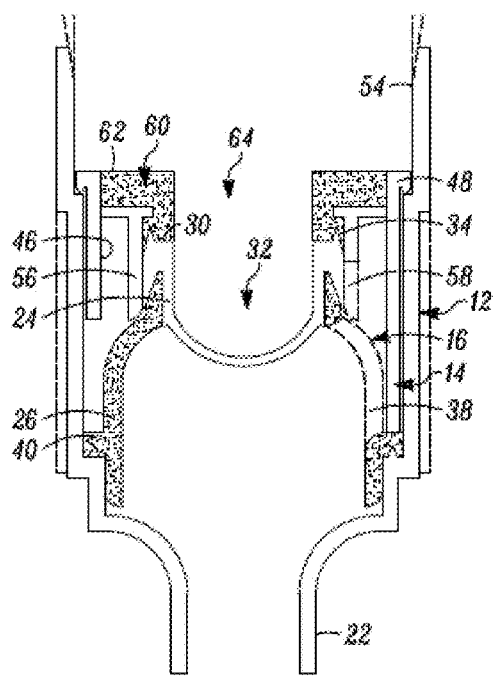
FIG. 3 is a cross-sectional view of the valve of FIG. 1, in the closed position.
Figure 4:
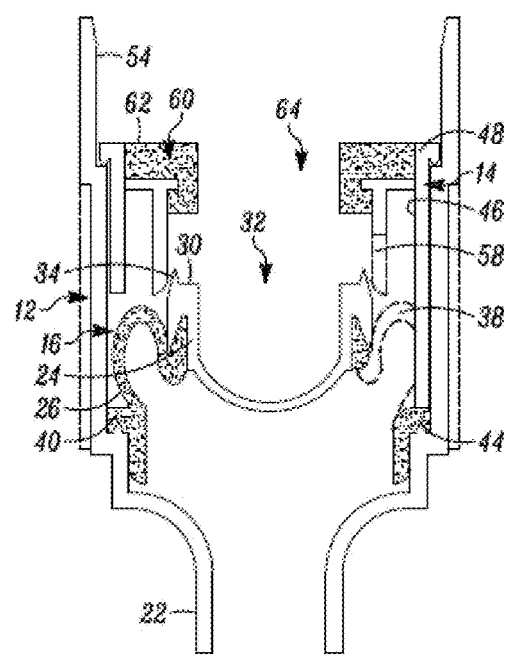
FIG. 4 is a cross-sectional view of the valve of FIG. 1, in the open position.

As shown in FIG. 2, the flexible valve member 16 comprises an upper substantially cylindrical shaped portion 24 atop a lower approximately dome or spherical-shaped portion 26. The upper portion 24 of the flexible valve member 16 is rigid relative to the lower portion 26. In the illustrated embodiment, the upper portion 24 is over-molded atop the lower portion 26. The upper substantially cylindrical shaped portion 24 defines a substantially cylindrical sidewall 28 and a top surface 30. The sidewall 28 functions as a cylindrical sealing surface, as described further below. The upper portion 24 further defines an axially extending socket 32, axially extending downwards into the upper portion from the top surface 30 for mating with a filling device 70, as described further below. In some embodiments, as shown in FIGS. 3 and 4, the upper portion 24 may further include an annular retaining member 34, axially extending upwards from the top surface 30, for sealingly engaging an adjacent septum 60 of the valve body 14 when in the closed position, as described further below.

The lower approximately dome or spherical-shaped portion 26 defines an integral spring 36. In some embodiments, the lower portion 26 is made of an elastomeric flexible material such as silicone and glass filled polybutylene terephthalate (PBT) or a silicone blend. However, as may be recognized by those of ordinary skill in the pertinent art based on the teachings herein, the lower approximately dome or spherical-shaped portion may take any of numerous different shapes and/or configurations, or may be formed of any of numerous different materials, that are currently known, or that later become known, for performing the function of the integral spring as described herein. The integral spring 36 of the lower approximately dome or spherical-shaped portion 26 allows the flexible valve member 16 to move axially between a normally closed position, as shown in FIG. 3, and an open position, as shown in FIG. 4. The integral spring 36 naturally biases the flexible valve member 16 into the normally closed position, where the cylindrical sealing surface 28 of the substantially cylindrical upper portion 24 sealingly engages a corresponding cylindrical valve seat 56 of the valve body 14 (described further below) to form a fluid-tight seal therebetween, thereby preventing the flow of substance into and/or out of the chamber 20, and hermetically sealing a substance contained within the chamber from the ambient atmosphere. The flexible valve member 16 may be depressed into the open position, where the cylindrical sealing surface is moved out of engagement with the cylindrical valve seat 56 and, in turn, permits the passage of substance therethrough to both introduce the substance into the chamber 20, as shown by the arrows in FIG. 4, and/or dispense the substance therefrom.

The lower portion 26 includes a flow aperture 38 to allow the flow of substance therethrough when in the open position. However, as may be recognized by those of ordinary skill in the pertinent art based on the teachings herein, the lower portion 26 may include any desired number of flow apertures, and the apertures may take any of numerous different configurations in order to, for example, achieve the desired flow of substance into and/or out of the chamber 20. The lower portion 26 further includes an annular flange 40 laterally projecting therefrom, proximally adjacent a lower end of the lower portion. The annular flange 40 defines an annular recess 42 in a bottom end thereof for sealingly receiving a corresponding first annular retaining member 44 of the shell 12, to sealingly mount the flexible valve member 16 within the shell 12. In the illustrated embodiment, the first annular retaining member 44 is in the form of an annular spike. However, as may be recognized by those of ordinary skill in the pertinent art based on the teachings herein, the retaining member may take any of numerous different configurations that are currently known, or that later become known, for sealingly engaging the annular flange of the flexible valve member.

As illustrated in FIG. 1, the valve body 14 is sealingly mounted atop the flexible valve member 16 within the shell 12. In some embodiments, the valve body 14 is made of silicone and glass filled (PBT) or polypropylene and a silicone blend. However, as may be recognized by those of ordinary skill in the pertinent art based on the teachings herein, the valve body may be formed of any of numerous different materials that are currently known, or that later become known. In the illustrated embodiment, the valve body 14 is substantially hollow and cylindrical, having a substantially cylindrical sidewall 46. As shown in FIG. 2, the valve body 14 includes an annular flange 48 laterally projecting from an upper end of the sidewall 46. The annular flange 48 defines an annular recess 50 in a bottom end thereof for sealingly receiving a corresponding second annular retaining member 52 of the shell 12, to sealingly mount the valve body 14 within the shell 12, atop the flexible valve member 16. In the illustrated embodiment, the second annular retaining member 52 is in the form of an annular spike. However, as may be recognized by those of ordinary skill in the pertinent art based on the teachings herein, the retaining member may take any of numerous different configurations that are currently known, or that later become known, for sealingly engaging the annular flange of the valve body.

In the illustrated embodiment, the second annular retaining member 52 of the shell 12 is axially recessed from an upper end of the shell 12. Consequently, when the valve body 14 is mounted therein, an upper end of the valve body 14 is correspondingly axially recessed from the upper end of the shell 12, thereby defining a portion of the sidewall of the shell 12, from the upper end of the valve body 14 to the upper end of the shell 12, as an axially-extending ledge 54. When the valve body 14 is mounted, the lower end of the cylindrical sidewall 46 of the valve body presses onto the top end of the laterally projecting annular flange 40 of the flexible valve member 16, thereby ensuring a sealing fit between the annular flange 40 and the first annular retaining member 44 of the shell 12.

As shown in FIG. 2, the valve body 14 further includes a central cylindrical valve seat 56, axially recessed from the upper end of the valve body, and axially extending downward. The valve seat 56 sealingly engages the cylindrical sealing surface 28 of the flexible valve member 16, to form a fluid-tight seal therebetween when the flexible valve member 16 is in the closed position, as described above. The cylindrical valve seat 56 defines a flow aperture 58 therethrough, configured be in fluid communication with the flow aperture 38 of the valve member 16 when the valve member is in the open position, to allow the flow of substance therethrough. As may be recognized by those of ordinary skill in the pertinent art based on the teachings herein, the valve seat 56 may include any desired number of flow apertures 58, and the apertures may take any of numerous different configurations in order to, for example, achieve the desired flow of substance into and/or out of the chamber 20.

The upper end of the valve body 14 further defines an annular recess for fittingly receiving a septum 60 atop the axially-recessed cylindrical valve seat 56. In the illustrated embodiment, the septum 60 is over-molded into the annular recess and defines a top surface, flush with the top surface of the valve body, together defining a stop surface 62 of the valve body 14, as shown in FIG. 2. A bottom end of the septum 60 sealingly engages the top surface 30 of the upper portion 24 when the flexible valve member 16 is in the closed position, as described above. As shown in FIG. 2, the septum 60 also defines a septum passageway 64 axially extending therethrough. The septum passageway 64 is configured to align with the axially extending socket 32 of the upper portion 24 of the valve member 16, and is of substantially equal diameter thereto, for allowing the filling device 70 to pass therethrough and mate with the socket 32. In some embodiments, the septum 60 is made of an elastomeric material. However, as may be recognized by those of ordinary skill in the pertinent art based on the teachings herein, the septum may be formed of any of numerous different materials that are currently known, or that later become known, for performing the function of the septum as described herein.

Figure 5:
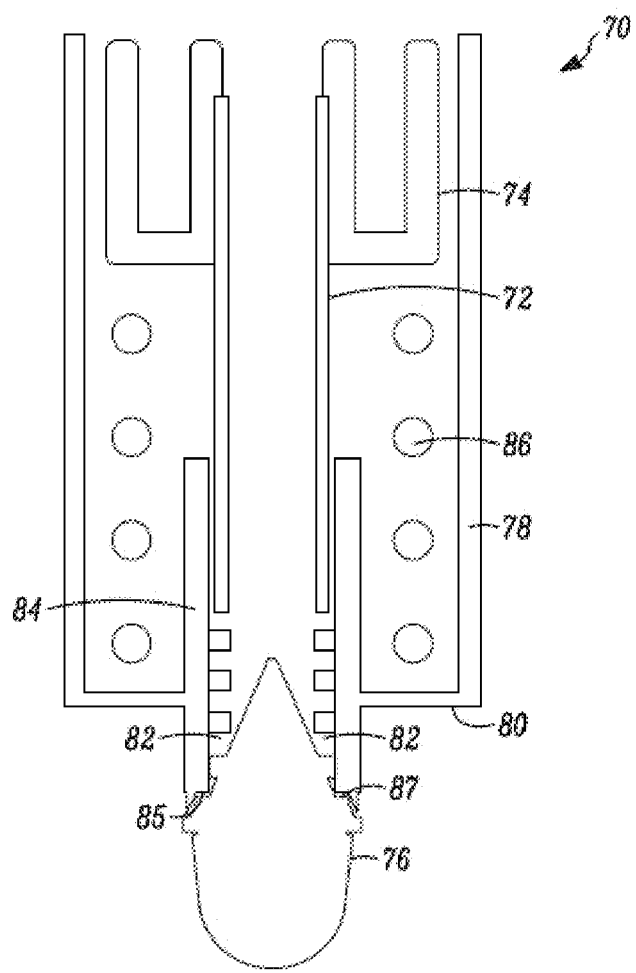
FIG. 5 is a cross-sectional view of a corresponding filling member engageable with the valve of FIG. 1.

In FIG. 5, a filling device for mating with the valve 10, in accordance with another embodiment, is indicated generally by the reference numeral 70. An exemplary embodiment of a filling device is disclosed in U.S. Provisional Patent Application No. 61/659,382, filed Jun. 13, 2012, entitled "Device with Penetrable Septum, Filling Needle and Penetrable Closure, and Related Method" and similarly titled U.S. Provisional Patent Application No. 61/799,744, filed Mar. 15, 2013, and U.S. patent application Ser. No. 13/450, 306, filed Apr. 18, 2012, entitled "Needle with Closure and Method," which, in turn claims benefit of U.S. Provisional Application No. 61/476,523, filed Apr. 18, 2011, entitled "Filling Needle and Method," all of which are hereby expressly incorporated by reference in their entireties as part of the present disclosure as if fully set forth herein. In the illustrated embodiment, the filling device 70 is a cannula. However, as may be recognized by those of ordinary skill in the pertinent art based on the teachings herein, the filling device may define any of numerous filling devices that are currently known, or that later become known, capable of performing the function of the filling device as described herein, such as, for example, a probe. The filling device 70 comprises a hollow shaft 72, a plunger 74 engaging the hollow shaft 72 at a proximal end thereof, a tip 76 formed at an opposing distal end thereof, and a surrounding closure 78, having a distal surface 80. The hollow shaft 72 defines two flow ports 82 in fluid communication with the interior of the hollow shaft. In the illustrated embodiments, the two ports are diametrically opposed relative to each other. However, as may be recognized by those of ordinary skill in the pertinent art based on the teachings herein, the shaft may define any number of ports that may define any of numerous different configurations and locations. A proximal end of the filling device 70 may be attached to a filling line or tubing (not shown), for deploying a substance into the shaft 72. As may be recognized by those of ordinary skill in the pertinent art based on the teachings herein, any of numerous different types of fittings or connections that are currently known, or that later become known, may be employed for connecting the filling device to a filling or other type of line, tube or conduit.

Figure 6A:
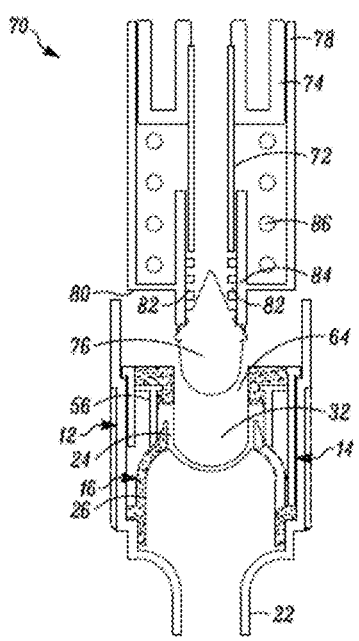
FIGS. 6A through 6C are sequential cross-sectional views of the filling member of FIG. 5 mating with the valve of FIG. 1 for filling a device or chamber attached thereto through the valve.

In the illustrated embodiment, the closure 78 is axially slideable, having an internal central cylindrical shutter 84 located at a distal end thereof, that slides axially over the shaft 72 and the flow ports 82. The shutter 84 projects from inside the distal end of the closure 78 to the tip 76 of the shaft 72 to seal off the ports 82 from the ambient atmosphere. In the illustrated embodiment of FIG. 6B, the shutter 84 projects out of the distal surface 80 of the closure a distance approximately equivalent to the length of the septum passageway 64. The closure 78 and/or the shaft 72 is movable between (i) a first position, wherein the cylindrical shutter 84 closes the ports 82, as shown in FIG. 6A, and (ii) a second position, wherein the cylindrical shutter 84 is displaced away from the ports 82, thereby opening the ports, as shown in FIG. 6C. In the first position, the shutter 84 forms a substantially fluid-tight seal between the ports 82 and the ambient atmosphere. A distal end of 85 of the shutter 84 is engageable with an annular stop surface 87 of the shaft tip 76 to stop the closure and shutter in the first or closed position.

In the illustrated embodiment of FIG. 5, the closure 78 extends both annularly and axially about the shaft 72 and the plunger 74, and is slidably mounted thereon. The filling device 70 further includes a coil spring 86 mounted within the closure 78, between a distal end of the plunger 74 and the distal surface 80 of the closure. The spring 86 biases the closure in the direction from the second or open position to the first or closed position to normally close the ports 82. However, as may be recognized by those of ordinary skill in the pertinent art based on the teachings herein, the closure may be biased in any of numerous different ways that are currently known or that later become known, and if a spring is used, any of numerous different springs or combinations of springs may be used. As also may be recognized by those of ordinary skill in the pertinent art based on the teachings herein, the closure may take any of numerous different configurations that are currently known, or that later become known, for performing the function of the closure as described herein.

Figure 6B:
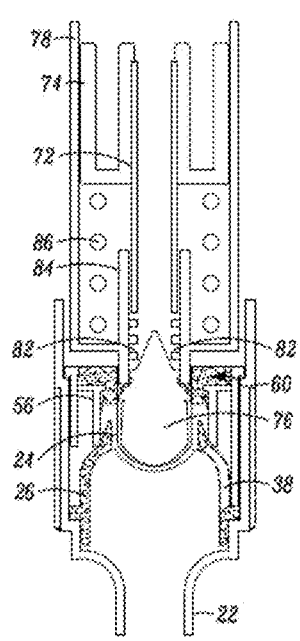
Figure 6C:
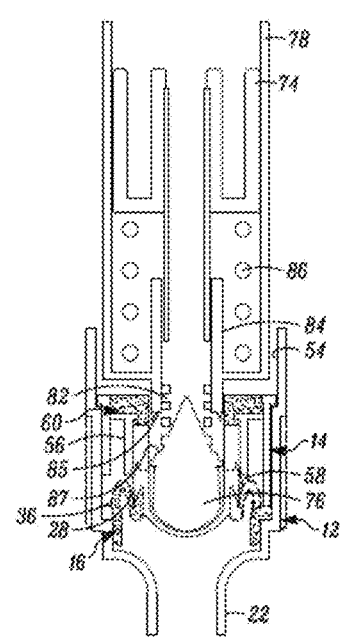

As shown in the illustrated embodiment of FIGS. 6B and 6C, the filling device 70 mates with the valve 10 to aseptically or sterile fill fluids through the valve 10 and into the chamber 20 of the container 18. In the illustrated embodiment, the filling device 70 is slidably engageable with the shell 12 of the valve 10. When the distal surface 80 of the closure 78 engages the stop surface 62 of the vial body 14, the smooth tip 76 fully mates with the axially extending socket 32. In the illustrated embodiment, the closure 78 of the filling device 70 is stabilized in part by the axially-extending ledge 54 of the shell 12, when the distal surface 80 engages the stop surface 62. However, as may be recognized by those of ordinary skill in the pertinent art based on the teachings herein, the filling device 70 may engage the valve 10 in any of numerous different ways, that are currently known or that later become known, such as, for example, by snapping onto or into the valve, or alternatively by threadedly connecting to the valve.

In the illustrated embodiment, the smooth tip 76 is defined by a smooth bulbous tip which mates with the axially extending socket 32. However, as may be recognized by those of ordinary skill in the pertinent art based on the teachings herein, the filling device tip and the axially extending socket of the valve may define any of numerous other configurations that mate together, that are currently known, or that later become known.

As shown in FIG. 6A, prior to mating with the valve 10, and when the filling device tip 76 is exposed to the ambient atmosphere, the closure 78 is in the closed position, wherein the cylindrical shutter 84 is sealing the ports 82 with respect to ambient atmosphere to thereby maintain the sterility of the ports and of the interior of the filling device. As shown in FIG. 6B, when the distal surface 80 of the closure 78 engages the stop surface 62 and the tip 76 mates with the socket 32, the cylindrical shutter 84 is interposed between the ports 82 and the septum 60 to substantially prevent contact between the ports and the septum. In this position, the stop surface 62 of the valve body 14 prevents further axial movement of the closure 78 and the shutter 84. Thereafter, when the plunger 74 is axially depressed, as shown in FIG. 6C, the shaft 72 and the tip 76 move axially relative to the closure 78 and the shutter 84, against the bias of the spring 86, from the first, or closed, position to the second, or open, position, thereby opening the ports 82. The tip 76 also simultaneously displaces the flexible valve member 16 from the closed position to the open position. In the open position of both the ports 82 and the flexible valve member 16, fluid within the filling device is permitted to flow through the open ports, through the flow aperture(s) 58 in the valve seat 56 and through the flow aperture(s) 38 in the lower portion 26 of flexible valve member 16, and into the chamber 20. Since the sterile ports 82 are not exposed to the ambient atmosphere, the ports, interior of the filling device, and fluid flowing therethrough, are never contaminated and/or are maintained sterile as the fluid is dispended into the chamber 20.

After the chamber 20 is filled as desired, the steps shown in FIGS. 6A-6C are generally reversed and the filling device 70 is withdrawn from the valve 10. First the plunger 74 is released, and the spring 86 naturally rebounds and biases the plunger 74, the shaft 72 and the tip 76, away from the valve 10, in the direction from the second position to the first position. Both the shaft 72 and the flexible valve member 16 return to their closed, sealed, positions, where the shutter 84 again forms a substantially fluid-tight seal between the ports 82 and the ambient atmosphere, and the cylindrical sealing surface 28 of the flexible valve member 16 reengages the cylindrical valve seat 56 to form a fluid-tight seal therebetween. Thereafter, the filling device 70 is withdrawn and disengaged from the valve 10. Thus, during, upon, and, in some embodiments, before withdrawal of the filling device 70 from the valve 10, the shutter 84 recloses the ports 82 to prevent any contamination of the ports 82 or interiors of the filling device, and the flexible valve member 16 recloses to prevent any contamination of the interior of the valve 10 and/or chamber 20.

One advantage of the present invention is that the filling device, such as the cannula in the illustrated embodiment, defines a smooth tip. This is safer for use than a filling device with a sharp tip, which may cause injury. Further, the filling device does not pierce through the stopper of the valve but rather depresses the flexible valve member from a closed position to an open position. Thus, there is no chance for any septum material to dislodge and contaminate the substance within the attached container or device. In addition, there is no resulting aperture from penetration of the valve requiring resealing after the filling device is disengaged. Rather, the filling device naturally springs back into the closed and sealed position.

In FIGS. 7-11, another device is indicated generally by the reference numeral 100. The connector 100 is substantially similar to the valve 10 and filling device 70 described above in connection with FIGS. 1-6, and therefore like reference numerals preceded by the numeral "1" are used to indicate like elements. A primary difference of the connector 100 in comparison to the valve 10 and filling device 70, is that the valve 10 comprises a portion of a first or female connector 110, and the filling device 70 comprises a portion of a second or male connector 170, forming an aseptic self-closing connector. An exemplary embodiment of an aseptic self-closing connector is disclosed in co-pending U.S. patent application Ser. No. 13/864,919, filed Apr. 17, 2013, entitled "Self Closing Connector," which, in turn claims benefit of similarly titled U.S. Provisional Application No. 61/625,663, filed Apr. 17, 2012, U.S. Provisional Application No. 61/635,258, filed Apr. 18, 2012, and U.S. Provisional Application No. 61/784,764, filed Mar. 14, 2013, each of which is hereby expressly incorporated by reference in its entirety as part of the present disclosure.

Figure 7:
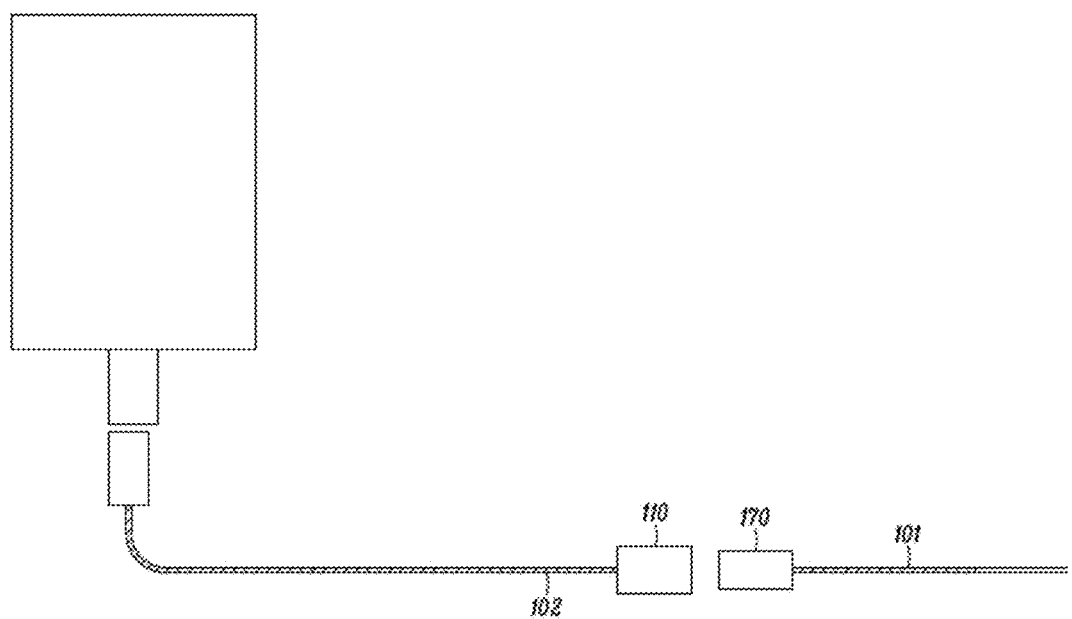
FIG. 7 is a schematic view of another embodiment of a valve comprising a portion of a female connector, and another embodiment of a filling member, comprising a portion of a male connector, for connecting together and transferring fluid therethrough.
Figures 10A, 10B, 10C:
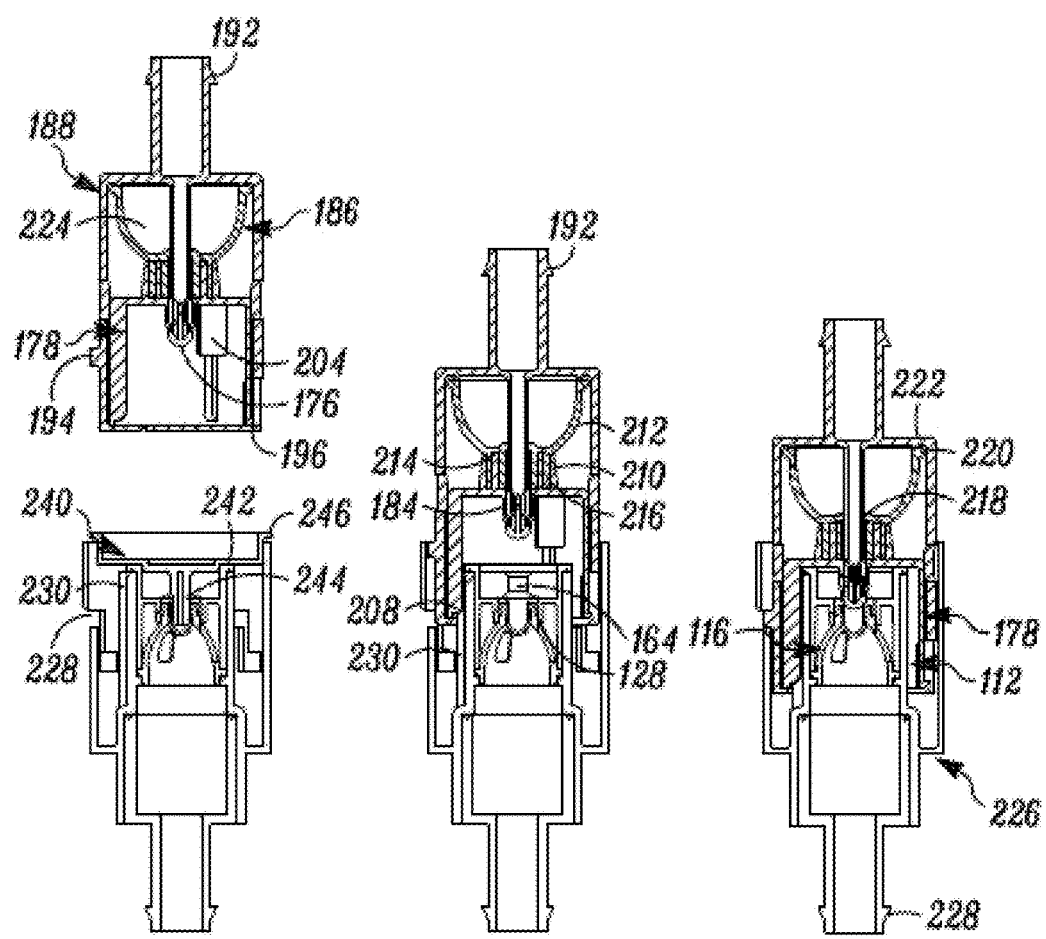
FIGS. 10A through 10F are sequential cross-sectional views of the male and female connectors of FIG. 7, showing the male connector from alignment and engagement with the female connector, to full connection with the female connector, for transferring fluid therethrough.

In the illustrated embodiment, the male connector 170 comprises a male shell 188, having a filling member 190, a closure 178, and a spring element 186. As shown in FIG. 10A, the male shell 188 comprises a central first hollow shaft 172, with a tip 176 formed at a dispensing end of the shaft, two ports 182, 182, proximally displaced from the tip 176 of the shaft in fluid communication with the interior of the first hollow shaft 172, and a barbed fitting 192 protruding from the hollow shaft at an inlet end thereof, for engaging a fluid line 101 (as shown in FIG. 7). In the illustrated embodiment, the filling member tip 176 is defined by a substantially bulbous tip; however, as may be recognized by those of ordinary skill in the pertinent art based on the teachings herein, the tip may define any of numerous other blunt or substantially curvilinear tip configurations that are currently known, or that later become known. In the illustrated embodiment, the two ports 182 are diametrically opposed relative to each other; however, as may be recognized by those of ordinary skill in the pertinent art based on the teachings herein, the filling member may define any number of ports that may define any of numerous different configurations and locations. In the illustrated embodiment, the filling member 190 is integrally molded with the male shell 188; however, as may be recognized by those of ordinary skill in the pertinent art based on the teachings herein, the filling member may be fixedly attached to the male shell in any of numerous other configurations that are currently known, or that later becomes known.

Figure 8:
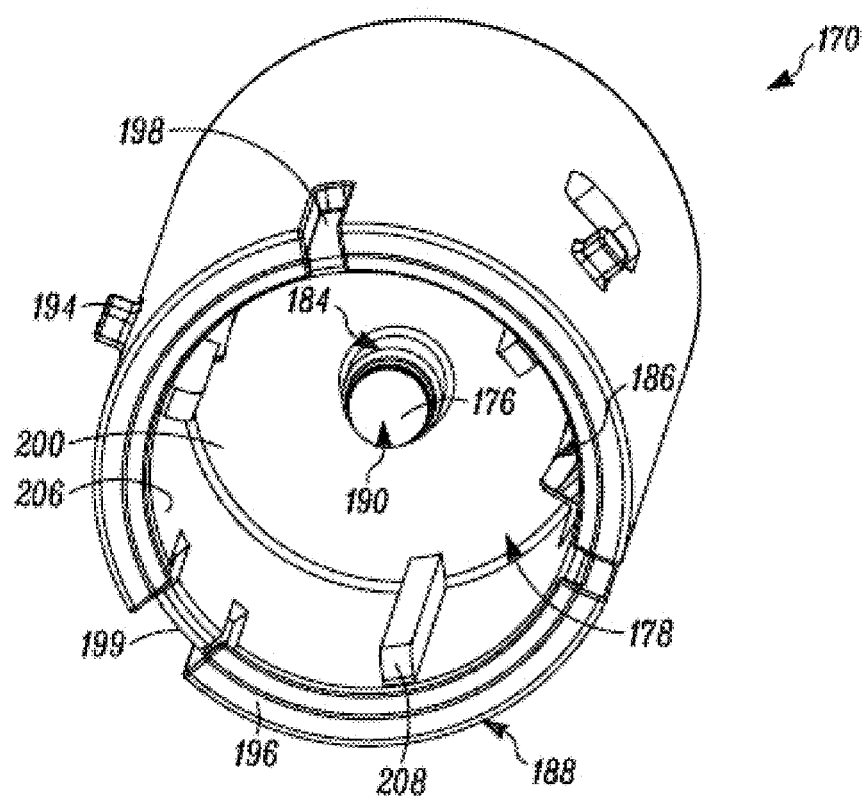
FIG. 8 is a perspective view of the male connector of FIG. 7.

As shown in FIG. 8, the male connector includes lugs 194 laterally extending outwardly from the male shell 188, for engaging corresponding primary receiving slots 228 (shown in FIG. 9) in the female connector 110, as described further below. The lugs 194 are proximally offset from a distal end 196 of the male connector 170 that engages the female connector 110. The male connector also defines axially-extending slots 198, extending from the distal end 196 of the male connector, as shown in FIG. 8, for receiving therein an alignment tab 199 of the closure 178, as described further below.

In the illustrated embodiment the cylindrical closure 178 is mounted within the cylindrical male shell 188, and includes a central cylindrical shutter 184, axially-extending from a rear wall 200 of the closure. The shutter 184 receives a portion of the filling member 190 including the ports 182 and extends both annularly and axially thereabout. The closure 178 is both rotatable and axially moveable with respect to the male shell 188. The closure 178 and/or the male shell 188 is axially movable between (i) a first position wherein the shutter 184 closes the ports 182, as shown typically in FIGS. 10A-10D, and (ii) a second position opening the ports 182, as shown typically in FIGS. 10E-10F. In the illustrated embodiment, the shutter 184 forms a substantially fluid-tight seal between the ports 182 and ambient atmosphere when in the first position. The closure 178, and thus the shutter 184, is biased by the spring element 186 in the direction from the second or open position to the first or closed position to normally close the ports 182, thereby preventing exposure of the ports 182, the interior of the first hollow shaft 172, and any fluid therein to the ambient atmosphere.

The male connector 14 also includes ribs 202, projecting inwardly from the interior wall of the male shell 188 and abutting the rear wall 200 of the closure 178, to normally prevent the closure from moving from the first position toward the second position. The closure 178 includes corresponding slots 204 extending distally from the rear wall 200 thereof, for receiving said ribs. Only when the ribs 202 align with the slots 204, can the closure 178 axially move from the first position to the second position. The male shell 188 and the closure 178 must first be rotated with respect to one another, in order to align the ribs 202 with the slots 204, as explained further below.

As shown in FIG. 8 the closure 178 also includes the alignment tab 199, integrally formed with and along the cylindrical sidewall 206 of the closure, where a distal end of the alignment tab 199 is substantially flush with a distal end of the closure 178. When the alignment tab 199 engages one of the axially-extending slots 198 of the male shell 188, the closure and the male shell cannot rotate with respect to one another, and therefore the ribs 202 cannot be aligned with the slots 204. However, when the tab 199 is biased inwardly and disengaged from one of the slots 198, as described further below, the closure 178 and male shell 188 become rotatable with respect to one another.

The closure 178 also includes axially-extending projections 208, projecting inwardly from the cylindrical side wall 206 of the closure, for engaging secondary receiving slots 230 of the female connector 110, as explained further below. In the illustrated embodiment, the axially-extending projections 208, extend the entire length of the closure sidewall 206, but in other embodiments may not.

In the illustrated embodiment, as shown in FIGS. 10A-10F, the male connector 170 includes a substantially dome shaped spring element 186 that naturally biases the closure 178 in the direction from the second or open position to the first or closed position. As may be recognized by those of ordinary skill in the pertinent art based on the teachings herein, the closure may be biased in any of numerous different ways that are currently known or that later become known, and if a spring is used, any of numerous different springs or combinations of springs may be used, such as, for example, a coil spring as described in the embodiment of FIGS. 1-6 above. The substantially dome shaped spring element 186 is located within the male shell 110, extending between the rear wall of the male shell 188 and the rear wall of the closure 178, and the first hollow shaft 172 of the filling member 190 extends therethrough. The sprint element 186 comprises a cylindrical portion 210, atop a substantially dome-shaped portion 212. The cylindrical portion includes an annular sealing recess 214, for sealingly receiving a corresponding annular sealing projection 216 extending from of the rear wall 200 of the closure 178. In the illustrated embodiment, the spring element 186 is over molded onto the annular sealing projection 216 of the closure 178, to ensure a substantially fluid-tight seal between the cylindrical portion 210 of the spring element and the closure.

The substantially dome-shaped portion 212 of the spring element 186 is formed of a resilient and/or elastomeric material defining an integral spring therein. The integral spring can be manually compressed and maintained in the compressed state. Otherwise, the integral spring naturally rebounds and biases the closure 178 in a direction from the second or open position to the first or closed position. At the junction of the cylindrical portion 210 and the dome-shaped portion 212, the spring element 186 includes an inwardly-extending annular seal 218, sealingly engaging and slideable relative to the first hollow shaft 172 and vice versa. In the illustrated embodiment, the slideable seal is an O-ring, integrally formed with the spring element 186. However, as may be recognized by those of ordinary skill in the pertinent art based on the teachings herein, the slideable seal may take the form of any sealing member, currently known or that later becomes known, capable of sliding along and sealingly engaging the hollow shaft of the filling member and may not be integral with the spring element.

As shown in FIGS. 10A-10F, the opposing base end of the dome-shaped portion 212 includes an integrally formed annular one-way venting valve 220, which engages the rear wall of the male shell 188. The rear wall of the male shell includes corresponding venting holes 222, normally sealed by the valve 220. When the spring element 186 is compressed, the venting valve 220 displaces from the holes 222 due to pressure inside the dome-shaped chamber 224, and allows the venting of air in a single direction out of the chamber 224, out of the spring element 186, through the venting holes 222 and into the ambient atmosphere. When the pressure equalizes, the valve 220 resiliently returns to its sealing position on the holes 222. Thereafter, in similar fashion, in order to allow the spring element 186 to naturally rebound and not remain in the compressed position, the venting valve 220 allows the venting of air in a single direction through the venting holes 222, when a vacuum is present in the spring element 186, and into the chamber 224 of the spring element 186. As may be recognized by those of ordinary skill in the pertinent art based on the teachings herein, the one-way venting valve may take the form of any of numerous integral or non-integral valves, that are currently known or that later become known, capable of performing the function of the venting valve as described herein.

Figure 9:
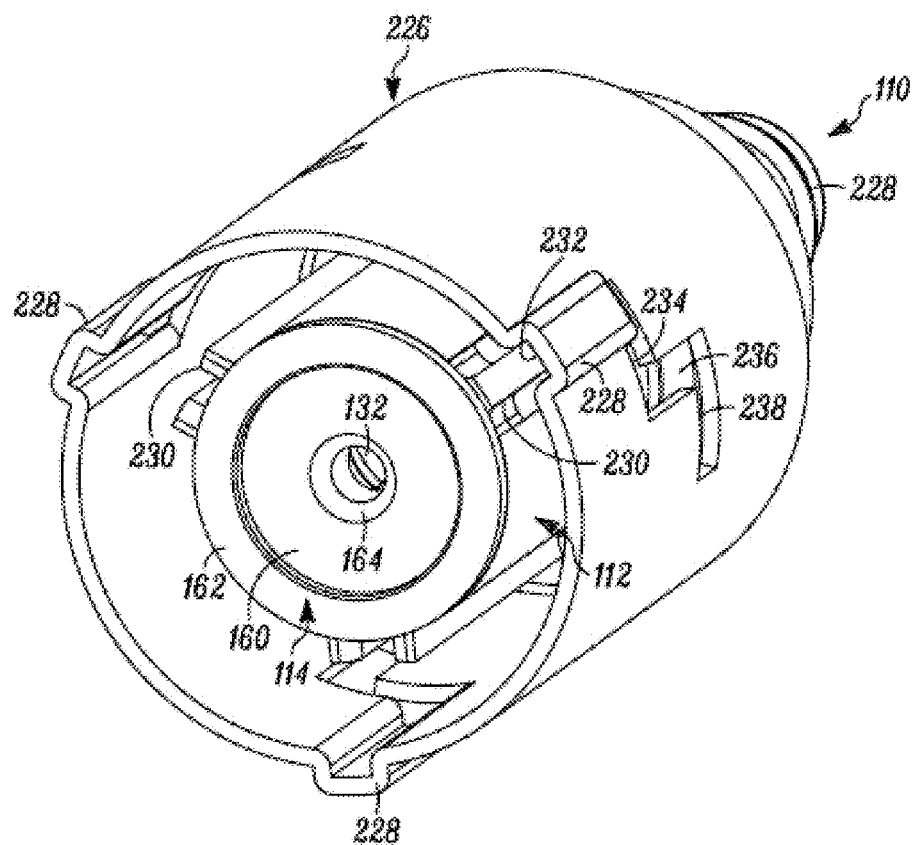
FIG. 9 is a perspective view of the female connector of FIG. 7.

As shown in FIG. 9, the female shell 226 comprises a central second shaft 112, or a chamber, therein, which receives the flexible valve member 116, the valve body 114 and the septum 160 therein, in the same manner as explained above with respect to the embodiment of FIGS. 1-6. In the illustrated embodiment, the second shaft or chamber 112 is integrally molded with the female shell 112; however, as may be recognized by those of ordinary skill in the pertinent art based on the teachings herein, the second hollow shaft may be fixedly attached to the female shell in any of numerous other configurations that are currently known, or that later become known. The second shaft 112 also includes an outwardly extending barbed fitting 228 at an outlet end thereof for connecting to a fluid line 102 (as shown in FIG. 7). As may be recognized by those of ordinary skill in the pertinent art based on the teachings herein, the second hollow shaft my include any of numerous fittings, that are currently known or that later become known, for engaging a fluid line.

As shown in FIG. 9, the female shell 226 further includes primary and secondary receiving slots 228, 230, for engaging the lugs 194 of the male shell 188 and the axially-extending projections 208 of the closure 178, respectively. The primary receiving slots 228 are part of the female shell 226 and the secondary receiving slots 230 are formed on the central second shaft 112. The secondary receiving slots 230 only extend axially. The primary receiving slots 228, on the other hand, include a first axially-extending portion 232, followed by a first substantially horizontal portion 234 a second axially-extending portion 236, and end with a second substantially horizontal portion 238. The first axially-extending portion 232 consists substantially of an outwardly projecting recess in the female shell wall. Alternatively, the portion 232 could be a window. The first substantially horizontal portion 234, second axially-extending portion 236, and second substantially horizontal portion 238 of the primary receiving slots 228 are formed by windows in the female shell wall. However, the portions 234, 236, and 238 may also be recesses.

As shown in FIG. 10A, a covering portion 240 is engageable with the female connector 110 when the male and female connectors are not connected. In the illustrated embodiment, the covering portion 240 is a substantially cylindrical cap. However, as may be recognized by those of ordinary skill in the pertinent art based on the teachings herein, the covering portion may take the form of any of numerous covering portions, configured to perform the function of the covering portion as described herein. The covering portion 240 is configured to sealingly engage the female shell 226. The covering portion 240 includes distal surface 242, which sealingly engages the stop surface 162 of the valve body 114 when the covering portion is placed on the female connector, and has a central axially-extending projection 244 projecting therefrom, configured to extend through the septum passageway 164 and mate with the axially-extending socket 132 of the flexible valve member 116. The covering portion 240 further includes an annular sealing surface 246, laterally projecting from an opposing proximal end of the covering portion, configured to mount atop the upper rim of the female shell 226 when the covering portion is placed on the female connector 110.

Figures 10D, 10E, 10F:
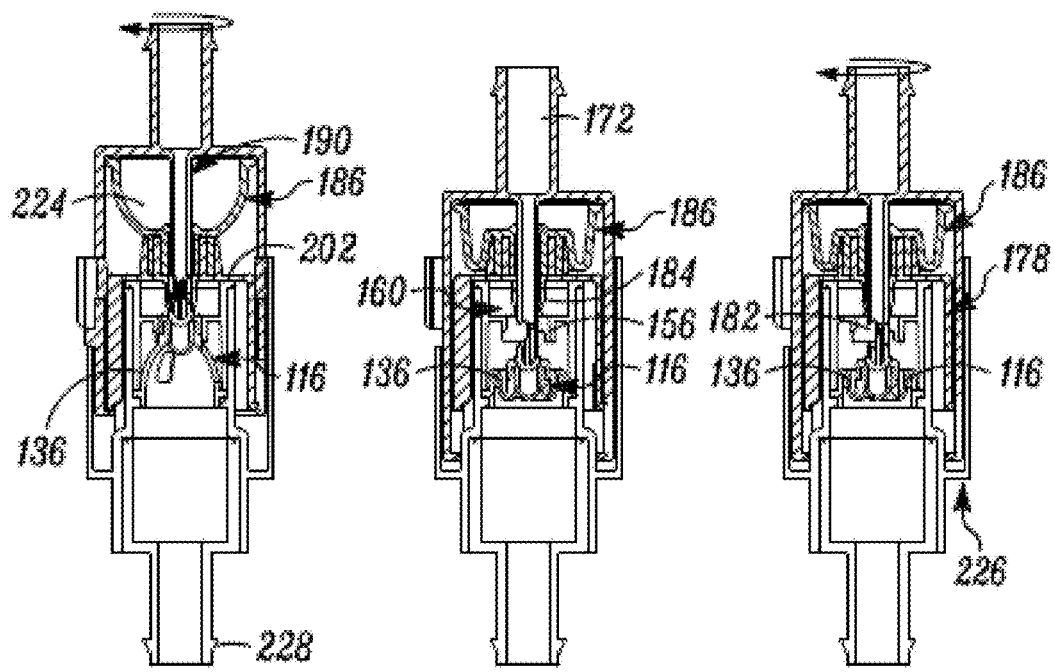
Figures 11A, 11B, 11C:
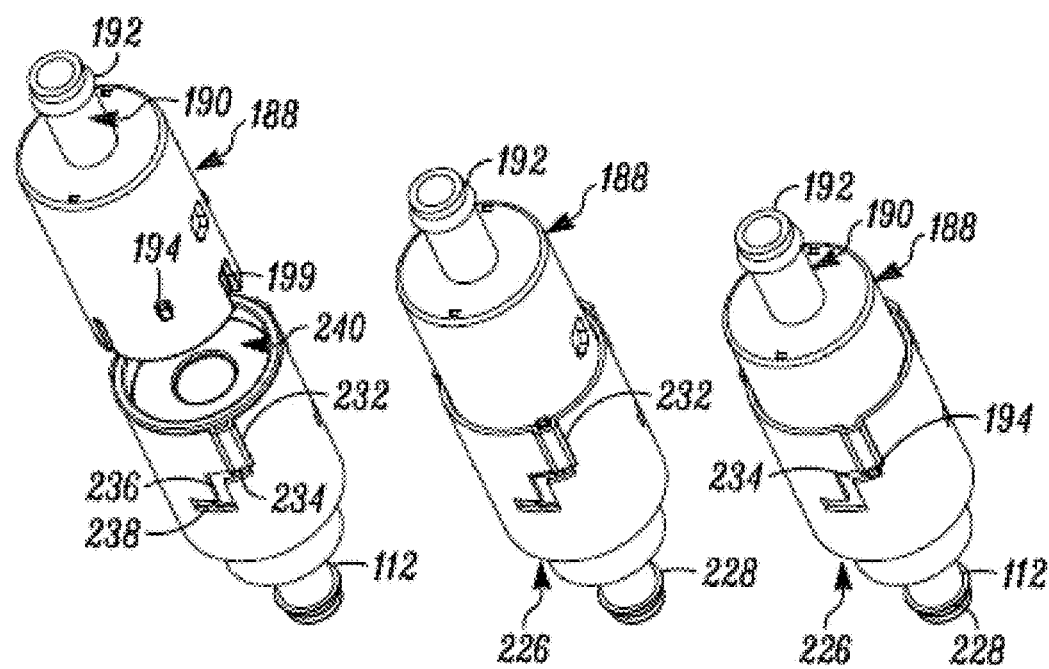
FIGS. 11A through 11F are sequential perspective views of the male and female connectors of FIG. 7, showing the male connector from alignment and engagement with the female connector, to full connection with the female connector, for transferring fluid therethrough.

As shown in FIGS. 10 and 11, the male and female connectors are connectable for the aseptic transfer of fluid therethrough. First, the covering portion 240 must be removed from engagement with the female connector 110. Then, the male connector 170 and female connector 110, which may be sterilized, are engaged, as shown typically in FIGS. 10B and 11B. In order to engage the male and female connectors, the alignment tab 199, must first align with one of the primary slots 228, as shown typically in FIGS. 10B and 11B. Otherwise the tab will catch on the edge of the female shell, and prevent engagement. The axially-extending projections 208 of the closure 178 and the lugs 194 of the male shell 188 are configured to also align with the primary and secondary slots 228, 230, respectively, when the alignment tab 199 aligns with one of the primary slots 228. As shown typically in FIGS. 10C and 11C, the male connector 170 is pressed further into engagement with the female connector 110 until the lugs 194 reach the end of the first axially-extending portion 232 of the primary slots 228, and the axially-extending projections 208 reach the end of the secondary slots 230. Because the lugs 194 are offset from the distal end of male shell 188, whereas the alignment tab 199 is substantially flush with the distal end of the closure 178, the alignment tab will reach the end of the first axially-extending portion 232 of the primary slots 228 prior to the lugs 194. Upon reaching this point, the alignment tab 199 is biased inwardly at the first substantially horizontal portion 234, and continues to slide against the inside of sidewall of the female shell 226 until the lugs 194 reach the end of the first axially-extending portion.

As the lugs 194 move down the first axially-extending portion 232 of the primary slots 228, the tip 176 of the filling member 190 correspondingly passes through the septum passageway 164. As shown typically in FIGS. 10A-10B prior to passage through the septum 160, the shutter 184 is in the closed position and cannot be opened, thereby sealing the ports 182 with respect to ambient atmosphere to maintain the sterility of the ports and of the interior of the filling member 190. As shown typically in FIG. 10C-10D, during passage through the septum 160 the shutter 184 remains in the closed position, and is still interposed between the ports 182 and the septum 160 to substantially prevent contact between the ports and the septum. The tip 176 of the filling member 190 engages the axially-extending socket 132 of the flexible valve member 116 when the lugs 194 reach the end of the first axially-extending portion 232, as shown in FIG. 10C.

Figures 11D, 11E, 11F:
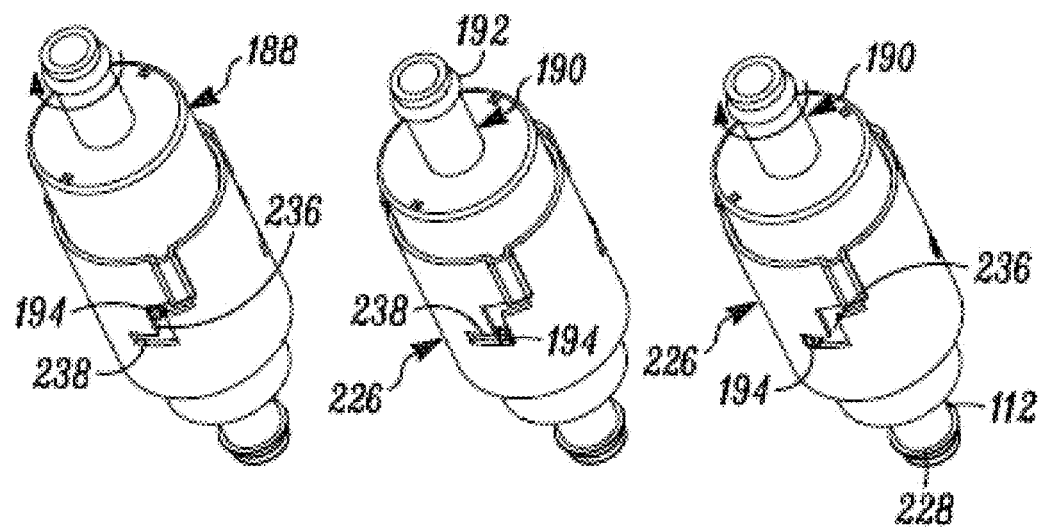

The male connector 170 is thereafter rotated to move the lugs 194 along the first substantially horizontal portion 234 of the primary slots 228, as shown in FIGS. 10D and 11D. Since the secondary slots 230 are solely axially-extending, and the axially-extending projections 208 of the closure 178 are engaged with the secondary slots 208, the closure 178 is prevented from also rotating relative to the female connector 110. However, because the alignment tab 199 of the closure 178 has been inwardly biased, thereby disengaging the tab from the corresponding axially-extending slot 198 of the male shell 188, the male shell is now rotatable relative to the closure 178. Consequently, the male shell 188, along with the filling member 190, rotates with respect to the stationary closure 178. Since the filling member 190 is only rotated in this step, and not moved further axially, the shutter 184 remains in the closed position, continuing to seal the ports 182 with respect to ambient atmosphere and to maintain the sterility of the ports and of the interior of the filling member 190.

Upon rotation to the end of the first substantially horizontal portion 234 of the primary slots 228, the ribs 202 of the male shell 188 and the corresponding slots 204 extending from the rear wall of the closure 178 align. Only then can the closure and/or the male shell be moved axially relative to one another to move the ports 182 into the second or open position. The male connector 170 is thus pressed into further axial engagement with the female connector 110, and the lugs 194 move down the second axially-extending portion 236, as shown in FIGS. 10E and 11E. Since the axially-extending projections 208 of the closure 178 have already reached the end of the secondary slots 230, the closure is prevented from further axial movement relative to the septum 160. Consequently, as the male shell 188 moves further into engagement with the female shell 226, as shown in FIG. 10E, the filling member 190 depresses the flexible valve member 116 from the closed position, where the valve seat 156 sealingly engages the sealing surface 128 of the flexible valve member, into the open position, where the sealing surface 128 is moved out of engagement with the valve seat 156. The closure 178 remains in place and compresses spring element 186, to, in turn, move the ports 182 past the end of the shutter 184 into the second or open position. As the ports are now past the septum, the septum seals the ports from the ambient atmosphere.

Upon reaching the end of the second axially-extending portion 236 of the primary slots 228, the male connector 170 is rotated again to slide the lugs 194 along the second substantially horizontal portion 238 of the primary slots, as shown in FIGS. 10F and 11F, to releasably lock the male and female connectors with the ports 182 in the second or open position, i.e., cannot be withdrawn, and the flexible valve member 116 in the open position. Alternatively, the portion 238 may not be present. In the open position of FIGS. 10F and 11F, fluid may travel from a fluid line 101, through the filling member 190, through the open ports 182, through the flow aperture(s) 158 in the valve seat 156, through the flow aperture(s) 138 of the flexible valve member 116, into the second shaft/chamber 112 of the female connector 110 and continuing to the fluid line 102. Since the sterile ports 182 are never exposed to the ambient atmosphere, the ports, interior of the filling member, and fluid flowing therethrough, are not contaminated and/or are maintained sterile as the fluid passes therethrough to the female connector 110.

To disconnect the male and female connectors 170, 110, the connecting steps are generally reversed. First, the male connector 170 is rotated to slide the lugs 194 in the reverse direction along the second substantially horizontal portion 238 (if present) of the primary slots 228, thereby unlocking the ports 182 from the open position. Upon reaching the opposing end of the second substantially horizontal portion and subsequent movement along portion 236, the spring element 186 naturally rebounds to return the ports 182 from the open position into the normally closed position, wherein the ports are again sealingly covered by the shutter 184. The shutter 184 remains interposed between the ports 182 and the septum 160 and therefore substantially prevents contact between the ports and the septum. The closed position is thereafter maintained, e.g., by the bias of the spring element 186 throughout the remainder of the disconnection process. Also as the lugs 194 move along the portion 236, the spring 136 of the flexible valve member 116 likewise simultaneously naturally rebounds to return the flexible valve member 116 from the open position, back into the normally closed position, where the sealing surface 128 thereof reengages the valve seat 156, and reseals the interior of the second shaft 112 and any fluid therein from the ambient atmosphere. The lugs 194 are moved back up the second axially-extending portion 236 of the primary slots 228 with the natural rebound of the sprint elements 136 and 186. Thereafter, the male connector 170 is rotated to move the lugs 194 along the first substantially horizontal portion 234 of the primary slots 228, returning the male connector 170 to its original configuration. The male connector 170 is then pulled out of engagement from the female connector 110, thereby withdrawing the tip 176 of the filling member 190 from the septum 160 and withdrawing the lugs 194 and the axially-extending projections 208 from the first axially-extending portion of the primary slots 228 and the secondary slots 230 respectively. The covering portion 240 may then be reengaged with the female connector 110.

The shutter 184 remains closed over the ports 182 and prevents contact between the ports and the septum 160 during withdrawal therefrom. Thus, during and upon, and in some embodiments, before, withdrawal of the filling member 190 from the septum 160, the shutter 184 maintains the ports 182 in the closed position and cannot be opened, thereby preventing any contamination of the ports or interior of the filling member.

The process may then be repeated whereby the male and female connectors are re-connected to aseptically transfer fluid therethrough once again. In some embodiments, the tip 176 of the filling member 190 may be re-sterilized prior to repeating connection of the two connectors. Sterilization and re-sterilization of the male and female connectors and/or any component parts therein may be achieved in accordance with the teachings in any of the following patents and patent applications, each of which is hereby expressly incorporated by reference in its entirety as part of the present disclosure: U.S. patent application Ser. No. 08/424,932, filed Apr. 19, 1995, entitled "Process for Filling a Sealed Receptacle under Aseptic Conditions," issued as U.S. Pat. No. 5,641,004; U.S. patent application Ser. No. 09/781,846, filed Feb. 12, 2001, entitled "Medicament Vial Having a Heat-Sealable Cap, and Apparatus and Method for Filling Vial," issued as U.S. Pat. No. 6,604,561, which, in turn, claims benefit of U.S. Provisional Patent Application No. 60/182,139, filed Feb. 11, 2000, entitled "Heat-Sealable Cap for Medicament Vial;" U.S. patent application Ser. No. 10/655,455, filed Sep. 3, 2003, entitled "Sealed Containers and Methods of Making and Filling Same," issued as U.S. Pat. No. 7,100,646, which, in turn, claims benefit of similarly titled U.S. Provisional Patent Application No. 60/408,068, filed Sep. 3, 2002; U.S. patent application Ser. No. 10/766,172, filed Jan. 28, 2004, entitled "Medicament Vial Having a Heat-Sealable Cap, and Apparatus and Method for Filling the Vial," issued as U.S. Pat. No. 7,032,631, which, in turn claims benefit of similarly titled U.S. Provisional Patent Application No. 60/443,526, filed Jan. 28, 2003 and similarly titled U.S. Provisional Patent Application No. 60/484,204, filed Jun. 30, 2003; and U.S. Provisional Patent Application No. 61/625,663, filed Apr. 17, 2012, entitled "Self Closing Connector."

In some embodiments, the septum 160 comprises a lower, i.e., base, layer having a relatively high durometer and an upper layer having a relatively lower durometer. In some such embodiments, the upper layer is not bondable with the lower layer and is over-molded thereon. In some such embodiments, the septum 160 may wipe the tip 176 of the filling member 190 and the shutter 184, of contaminants thereon during engagement and passage through the septum 160 by the tip 176, to prevent the tip and/or shutter from introducing such contaminants into the sterile interior of the female connector 110. The effectiveness of such wiping during piercing of the septum is dependent upon several factors, such as, for example, the wall thickness and durometer of the septum. In some embodiments, the durometer of the septum 160, or the layers thereof, is within the range of about 5 Shore A to about 65 Shore A, such as, for example, within the range of about 20 Shore A to about 50 Shore A. In some such embodiments, the durometer of the septum 160 is within the range of about 25 Shore A to about 45 Shore A. In some such embodiments the septum thickness is within the range of about ½ the diameter of the filling member to about double the largest diameter of the filling member. The present inventor has determined that the wiping effect on a tip surface by a septum having a wall thickness and durometer within said aforementioned ranges may achieve at least approximately a 3 log reduction in bio-burden when the male and female connectors are connected while immersed in a broth, which is about the reduction achieved by known UV pulse (5 second) sterilization techniques, to thereby at least partially sterilize the tip surface. Therefore, one advantage of the present invention is that it allows substantially sterile transfer of fluids within a non-aseptic, non-sterile or relatively low sterility assurance level ("SAL") environment (e.g., about 6 log bio-burden or lower).

It should be noted that any portion of the tip 176 of the filling member 190 that is not wiped by the septum 160 is never exposed in the interior of the second shaft 112. The tip 176 is sealingly engaged by the socket 132 prior to moving the flexible valve member 116 from the sealingly closed position to the open position, and remains in sealing engagement with the socket 132 throughout the entire time the flexible valve member 116 is in the open position, until the flexible valve member rebounds back into the sealingly closed position. Any portion of the tip 176 that is not wiped by the septum is sealingly covered by the socket 132 and never exposed to the interior of the second shaft 112. The tip 176 sealingly engages the socket 132, due to, in part, the corresponding shape of the socket 132 with respect to the shape of the tip 176 along with the downward directed force applied to the filling member 190 to engage the socket 132 in conjunction with the opposing upward directed spring force of the spring 136 of the flexible valve member.

Figure 12:
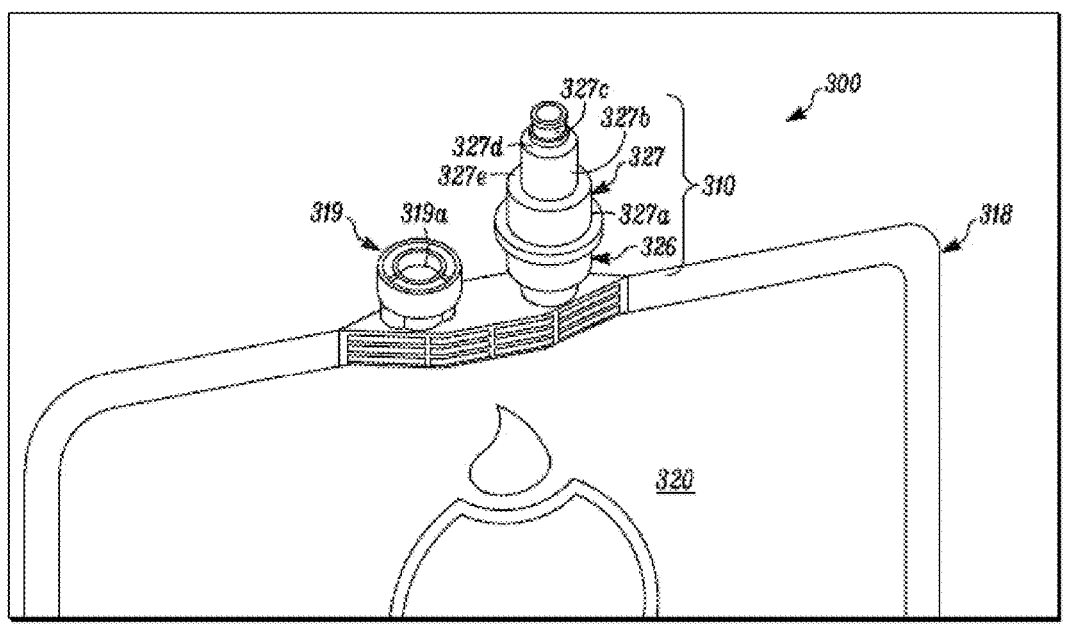
FIG. 12 is a perspective view of another embodiment of a valve comprising a portion of a connector coupled to a storage chamber for filling and dispensing fluids or other substances therefrom.
Figure 13A:
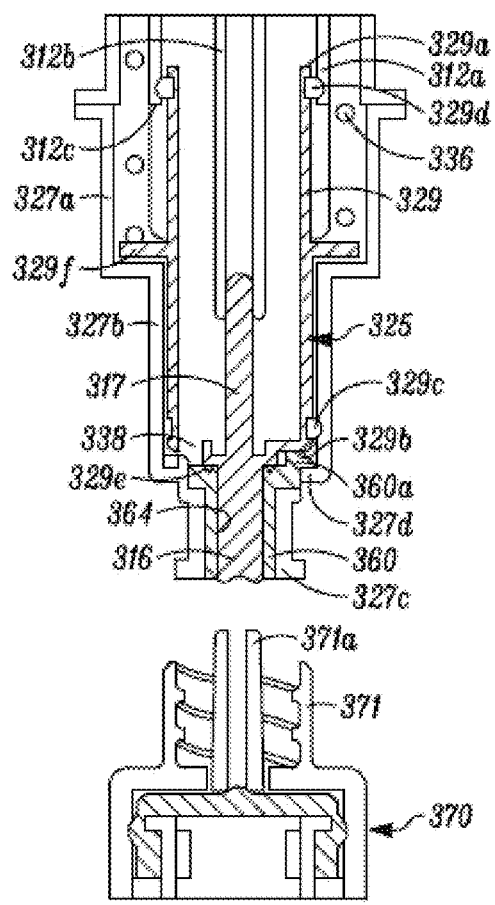
FIG. 13A is a cross-sectional partial view of the connector of FIG. 12 taken along the centerline of the connector, prior to engagement with a delivery device, with the valve in the first closed position.
Figure 13B:
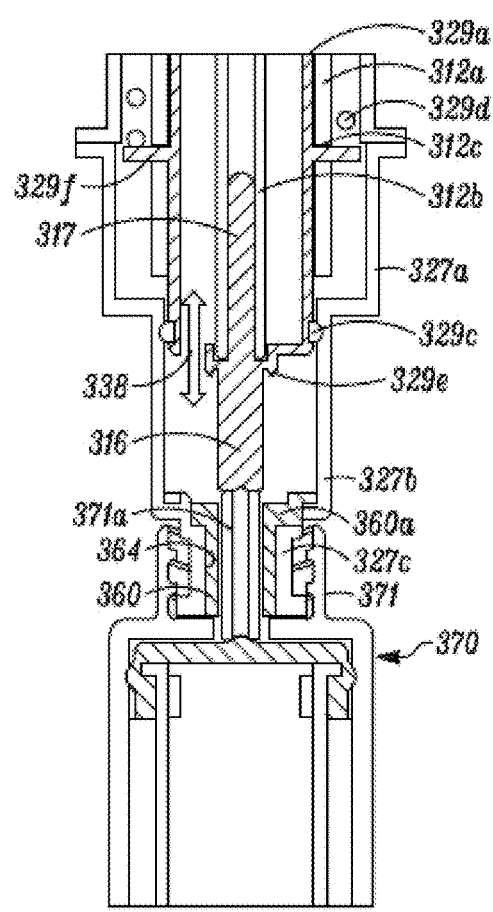
FIG. 13B is a cross-sectional partial view of the connector of FIG. 12 taken along the centerline of the connector, upon engagement with a delivery device, with the valve in the second open position.

In FIGS. 12-13B, another device is indicated generally by the reference numeral 300. The device 300 is substantially similar to the valve 10 and the connector 100 described above in connection with FIGS. 1-6, and 7-11, respectively. Therefore like reference numerals preceded by the numeral "3" are used to indicate like elements. As shown in FIG. 12, the device 300 comprises a bladder, bag, or pouch 318 defining a variable-volume storage chamber 320 therein and having first and second ports 319, 310, respectively, connected in fluid communication therewith.

As shown in FIG. 12, the first port 319 includes a penetrable and resealable septum 319a that is penetrable by a needle, filling or injection member (not shown) for sterile or aseptically filling the storage chamber 320 with substance to be stored therein. The septum 319a, in some embodiments, is formed of a material that is sufficiently elastic to close itself after withdrawal of the needle, filling or injection member therefrom to thereby ensure that the head loss left by a residual penetration hole after the injection member is withdrawn prevents fluid ingress therethrough. Although such a septum 319a is self-closing, the septum may be resealed by a liquid sealant such as silicone or a silicone-based sealant, and/or the application of radiation or energy thereto to hermetically seal the substance within the storage chamber 320 from the ambient atmosphere and thereby maintain the sterility of the substance.

For example, the septum 319a may be penetrable for sterile filling the variable-volume storage chamber 320 and resealable, such as by the application of laser, other radiation, or thermal energy, to hermetically seal the filled substance within the storage chamber 320 in accordance with the teachings of any of the following patents and patent applications, each of which is hereby expressly incorporated by reference in its entirety as part of the present disclosure: U.S. patent application Ser. No. 12/254,789, filed Oct. 20, 2008, entitled "Container Having a Closure and Removable Resealable Stopper for Sealing a Substance Therein and Related Method," which, in turn, claims the benefit of U.S. Patent Application No. 60/981,107, filed Oct. 18, 2007, entitled "Container Having a Closure and Removable Resealable Stopper for Sealing a Substance Therein;" U.S. patent application Ser. No. 12/245,678, filed Oct. 3, 2008, entitled "Apparatus For Formulating and Aseptically Filling Liquid Products," and U.S. patent application Ser. No. 12/245,681, filed Oct. 3, 2008, entitled "Method For Formulating and Aseptically Filling Liquid Products," which, in turn, claim the benefit of U.S. Patent Application No. 60/997,675, filed Oct. 4, 2007, entitled "Apparatus and Method for Formulating and Aseptically Filling Liquid Products;" U.S. patent application Ser. No. 12/875,440, filed Sep. 3, 2010, entitled "Device with Needle Penetrable and Laser Resealable Portion and Related Method," now U.S. Pat. No. 7,980,276, which is a divisional of U.S. patent application Ser. No. 12/371,386, filed Feb. 13, 2009, entitled "Device with Needle Penetrable and Laser Resealable Portion," now U.S. Pat. No. 7,810,529, which is a continuation of U.S. patent application Ser. No. 11/949,087, filed Dec. 3, 2007, entitled "Device with Needle Penetrable and Laser Resealable Portion and Related Method," now U.S. Pat. No. 7,490,639, which is a continuation of similarly titled U.S. patent application Ser. No. 11/879,485, filed Jul. 16, 2007, now U.S. Pat. No. 7,445,033, which is a continuation of similarly titled U.S. patent application Ser. No. 11/408,704, filed Apr. 21, 2006, now U.S. Pat. No. 7,243,689, which is a continuation of U.S. patent application Ser. No. 10/766, 172, filed Jan. 28, 2004, entitled "Medicament Vial Having a Heat-Sealable Cap, and Apparatus and Method for Filling the Vial," now U.S. Pat. No. 7,032,631, which is a continuation-in-part of similarly titled U.S. patent application Ser. No. 10/694,364, filed Oct. 27, 2003, now U.S. Pat. No. 6,805,170 which is a continuation of similarly titled U.S. patent application Ser. No. 10/393,966, filed Mar. 21, 2003, now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Patent Application No. 60/182,139, filed Feb. 11, 2000, and similarly titled U.S. Provisional Patent Application No. 60/443,526, filed Jan. 28, 2003, and similarly titled U.S. Provisional Patent Application No. 60/484,204, filed Jun. 30, 2003; U.S. patent application Ser. No. 13/193,662, filed Jul. 29, 2011, entitled "Sealed Contained and Method of Filling and Resealing Same," which is a continuation of U.S. patent application Ser. No. 12/791,629, filed Jun. 1, 2010, entitled "Sealed Containers and Methods of Making and Filling Same," now U.S. Pat. No. 7,992,597, which is a divisional of U.S. patent application Ser. No. 11/515,162, filed Sep. 1, 2006, entitled "Sealed Containers and Methods of Making and Filling Same," now U.S. Pat. No. 7,726,352, which is a continuation of U.S. patent application Ser. No. 10/655,455, filed Sep. 3, 2003, entitled "Sealed Containers and Methods of Making and Filling Same," now U.S. Pat. No. 7,100,646, which is a continuation-in-part of U.S. patent application Ser. No. 10/393,966, filed Mar. 21, 2003, entitled "Medicament Vial Having A Heat-Sealable Cap, and Apparatus and Method For Filling The Vial," now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Patent Application No. 60/182,139, filed on Feb. 11, 2000, and U.S. Provisional Patent Application No. 60/408,068, filed Sep. 3, 2002, entitled "Sealed Containers and Methods Of Making and Filling Same;" U.S. patent application Ser. No. 12/627, 655, filed Nov. 30, 2009, entitled "Adjustable Needle Filling and Laser Sealing Apparatus and Method," now U.S. Pat. No. 8,096,333, which is a continuation of similarly titled U.S. patent application Ser. No. 10/983,178, filed Nov. 5, 2004, now U.S. Pat. No. 7,628,184, which, in turn, claims the benefit of U.S. Provisional Patent Application No. 60/518,267, filed Nov. 7, 2003, entitled "Needle Filling and Laser Sealing Station," and similarly titled U.S. Provisional Patent Application No. 60/518,685, filed Nov. 10, 2003; U.S. patent application Ser. No. 11/901,467, filed Sep. 17, 2007 entitled "Apparatus and Method for Needle Filling and Laser Resealing," which is a continuation of similarly titled U.S. patent application Ser. No. 11/510,961 filed Aug. 28, 2006, now U.S. Pat. No. 7,270,158, which is a continuation of similarly titled U.S. patent application Ser. No. 11/070, 440, filed Mar. 2, 2005; now U.S. Pat. No. 7,096,896, which, in turn, claims the benefit of U.S. Provisional Patent Application No. 60/550,805, filed Mar. 5, 2004, entitled "Apparatus for Needle Filling and Laser Resealing;" U.S. patent application Ser. No. 12/768,885, filed Apr. 28, 2010, entitled "Apparatus for Molding and Assembling Containers with Stoppers and Filling Same," now U.S. Pat. No. 7,975,453, which is a continuation of similarly titled U.S. patent application Ser. No. 11/074,513, filed Mar. 7, 2005, now U.S. Pat. No. 7,707,807, which claims the benefit of U.S. Provisional Patent Application No. 60/551,565, filed Mar. 8, 2004, entitled "Apparatus and Method For Molding and Assembling Containers With Stoppers and Filling Same;" U.S. patent application Ser. No. 13/396,053, filed Feb. 14, 2012, entitled "Method for Molding and Assembling Containers with Stopper and Filling Same," which is a continuation of similarly titled U.S. patent application Ser. No. 12/715,821, filed Mar. 2, 2010, now U.S. Pat. No. 8,112,972, which is a continuation of similarly titled U.S. patent application Ser. No. 11/074,454, filed Mar. 7, 2005, now U.S. Pat. No. 7,669,390; U.S. patent application Ser. No. 11/339,966, filed Jan. 25, 2006, entitled "Container Closure With Overlying Needle Penetrable and Thermally Resealable Portion and Underlying Portion Compatible With Fat Containing Liquid Product, and Related Method," now U.S. Pat. No. 7,954,521, which, in turn, claims the benefit of U.S. Provisional Patent Application No. 60/647,049, filed Jan. 25, 2005, entitled "Container with Needle Penetrable and Thermally Resealable Stopper, Snap-Ring, and Cap for Securing Stopper;" U.S. patent application Ser. No. 12/861,354, filed Aug. 23, 2010, entitled "Ready To Drink Container With Nipple and Needle Penetrable and Laser Resealable Portion, and Related Method;" which is a divisional of similarly titled U.S. patent application Ser. No. 11/786,206, filed Apr. 10, 2007, now U.S. Pat. No. 7,780,023, which, into turn, claims the benefit of similarly titled U.S. Provisional Patent Application No. 60/790,684, filed Apr. 10, 2006; U.S. patent application Ser. No. 11/295,251, filed Dec. 5, 2005, entitled "One-Way Valve, Apparatus and Method of Using the Valve," now U.S. Pat. No. 7,322,491, which, in turn, claims the benefit of similarly titled U.S. Provisional Patent Application No. 60/644,130, filed Jan. 14, 2005, and similarly titled U.S. Provisional Patent Application No. 60/633,332, filed Dec. 4, 2004; U.S. patent application Ser. No. 12/789, 565, filed May 28, 2010, entitled "Resealable Containers and Methods of Making, Filling and Resealing the Same," which is a continuation of U.S. patent application Ser. No. 11/933,272, filed Oct. 31, 2007, entitled "Resealable Containers and Assemblies for Filling and Resealing Same," now U.S. Pat. No. 7,726,357, which is a continuation of U.S. patent application Ser. No. 11/515,162, filed Sep. 1, 2006, entitled "Sealed Containers and Methods of Making and Filling Same," now U.S. Pat. No. 7,726,352; U.S. patent application Ser. No. 13/045,655, filed Mar. 11, 2011, entitled "Sterile Filling Machine Having Filling Station and E-Beam Chamber," which is a continuation of U.S. patent application Ser. No. 12/496,985, filed Jul. 2, 2009, entitled "Sterile Filling Machine Having Needle Filling Station and Conveyor," now U.S. Pat. No. 7,905,257, which is a continuation of U.S. patent application Ser. No. 11/527,775, filed Sep. 25, 2006, entitled "Sterile Filling Machine Having Needle Filling Station within E-Beam Chamber," now U.S. Pat. No. 7,556,066, which is a continuation of similarly titled U.S. patent application Ser. No. 11/103,803, filed Apr. 11, 2005, now U.S. Pat. No. 7,111,649, which is a continuation of similarly titled U.S. patent application Ser. No. 10/600,525, filed Jun. 19, 2003, now U.S. Pat. No. 6,929, 040, which, in turn, claims the benefit of similarly-titled U.S. Provisional Patent Application No. 60/390,212, filed Jun. 19, 2002; U.S. patent application Ser. No. 13/326,177, filed Dec. 14, 2011, entitled "Device with Penetrable and Resealable Portion and Related Method," which is a continuation of similarly titled U.S. patent application Ser. No. 13/170, 613, filed Jun. 28, 2011, now U.S. Pat. No. 8,347,923, which is a continuation of U.S. patent application Ser. No. 12/401, 567, filed Mar. 10, 2009, entitled "Device with Needle Penetrable and Laser Resealable Portion and Related Method," now U.S. Pat. No. 7,967,034, which is a continuation of similarly titled U.S. patent application Ser. No. 11/933,300, filed Oct. 31, 2007, now U.S. Pat. No. 7,500, 498; U.S. patent application Ser. No. 13/329,483, filed Apr. 30, 2011, entitled "Ready to Feed Container," which is a continuation of International Application No. PCT/US2011/ 034703, filed Apr. 30, 2011, entitled "Ready to Feed Container and Method," which, in turn, claims the benefit of U.S. Provisional Patent Application No. 61/330,263 filed Apr. 30, 2010; and U.S. Provisional Patent Application No. 61/476,523, filed Apr. 18, 2011, entitled "Filling Needle and Method."

Alternatively, the septum 319a may be penetrable for sterile filling the variable-volume storage chamber 320 and resealable with a liquid sealant, such as a silicone sealant, to hermetically seal the filled substance within the storage chamber 320, in accordance with the teachings of any of the following patent applications, each of which is hereby expressly incorporated by reference in its entirety as part of the present disclosure: U.S. patent application Ser. No. 12/577,126, filed Oct. 9, 2009, entitled "Device with Co-Extruded Body and Flexible Inner Bladder and Related Apparatus and Method," which claims the benefit of similarly titled U.S. Provisional Patent Application No. 61/104, 613, filed Oct. 10, 2008; U.S. patent application Ser. No. 12/901,420, filed Oct. 8, 2010, entitled "Device with Co-Molded One-Way Valve and Variable Volume Storage Chamber and Related Method," which claims the benefit of similarly titled U.S. Provisional Patent Application No. 61/250,363, filed Oct. 9, 2009; and U.S. Provisional Patent Application No. 61/476,523, filed Apr. 18, 2011, entitled "Filling Needle and Method."

In the illustrated embodiment, the second port 310 is defined by a substantially cylindrical first shell 326 attached at a base end thereof to the pouch 318, and a second shell 327 secured at a base end thereof to the upper end of the first shell 326. The first shell 326 comprises a first hollow shaft 312a in fluid communication with the pouch 318 and a second, approximately central, hollow shaft 312b within the first hollow shaft. The upper end of the first shaft 312a (in the orientation in FIG. 12) is approximately flush with the upper end of the first shell 326. The second shaft 312b extends into the second shell 327.

The second shell includes a substantially cylindrical base portion 327a (secured to the first shell 326), a substantially cylindrical mid-portion 327b of different diameter, and an outer connector portion 327c of different diameter. In the illustrated embodiment, the connector portion 327c includes a male LUER connector. However, the connector portion 327c can take any suitable form of a connector, as should be appreciated by those of ordinary skill in the art. The outer portion 327c has a smaller diameter than the mid-portion 327b and therefore a first annular lip/shoulder 327d is defined at the interface therebetween. The mid-portion 310b has a smaller diameter than the base portion 310a, and therefore a second annular lip/shoulder 327e is formed at the interface therebetween. The diameter of the base portion 327a is substantially equal to the diameter of the first shell 326. The diameter of the mid-portion 327b is substantially equal to the diameter of the first shaft 312a. The first shell 326 and second shell 327 can be sealingly joined.

A septum or seat 360 is fittingly mounted into the outer portion 327c. In the illustrated embodiment, the septum 360 is over-molded or otherwise co-molded to the outer portion 327c, and an annular base thereof 360a is sealingly engaged with the corresponding annular lip 327d. The outer surface of the septum 360 is substantially flush with the outer surface of the outer portion 327c, and the septum 360 defines a septum passageway 364 therethrough. Similar to the embodiments above, the septum 360 is formed of an elastomeric material. However, as should be recognized by those of ordinary skill in the pertinent art based on the teachings herein, the septum may be formed of any of numerous different materials that are currently known, or that later become known, for performing the function of the septum or seat as described herein.

The second port 310 further includes a plunger 325 therein. The plunger 325 comprises a substantially hollow barrel 329, having an open base end 329a, and an upper surface 329b. The open base end 329a is slidably received within the first shaft 312a, and thus the inside of the barrel 329 is in fluid communication with the first shaft 312a, and, in turn, with the storage chamber 320. An approximately central elongated tip 316 extends from the upper surface 329a of the barrel 329. An approximately central member 317 extends from the upper surface 329b into barrel 329, and in sliding engagement with the second shaft 312b. The upper surface 329b of the barrel 329 defines at least one fluid-flow aperture 338 therein.

As shown in FIG. 13A, the barrel 329 further includes a first annular sealing member 329c, adjacent the upper surface 329b thereof, that sealingly engages the interior surface of the mid-portion 327b side-wall. The first annular seal 329c forms an interference fit with the substantially cylindrical interior surface of the mid-portion 327b and thereby forms a fluid-tight seal therebetween. The barrel 329 also includes a second annular sealing member 329d, adjacent the base end 329a thereof, that sealingly engages the interior surface of first shaft 312a side-wall. The second annular seal 329d forms an interference fit with the substantially cylindrical interior surface of the first shaft 312a and thereby forms a fluid-tight seal therebetween. In the illustrated embodiment, the sealing members 329c, 329d are formed by o-rings. Alternatively, the sealing members may be integrally formed with barrel 329, such as by forming annular protuberances thereon.

The plunger 325 is sealingly and slidably movable within the first shaft 312a of the first shell 326 and the second shell 327 between (i) a first position, as shown in FIG. 13A, wherein the elongated tip 316 extends through the passageway 364 of septum 360 and forms a seal therewith, and (ii) a second position, as shown in FIG. 13B, wherein the elongated tip 316 is retracted or displaced from the septum 360 and does not extend through or seal the passageway 364. Thus, in the first position, the tip 316 and the septum 360 define a closed, sealed, valve. The elongated tip 316 engages the septum 360 and forms a fluid-tight seal between the aperture(s) 338 and the ambient atmosphere, thereby closing the aperture(s) 338 from fluid flow therethrough. In some embodiments the septum 360 forms an interference fit with the tip 316 to thereby form the fluid-tight seal therebetween in the first position. Such interference fit is sufficiently small, though, to permit the elongated tip 316 to slide relative to the septum 360. The upper surface 329b of the barrel 329 also defines an annular spike 329e extending around the tip 316 that sealingly engages into the base end 360a of the elastomeric septum 360 in the first position for stabilization.

In the second position, the retracted tip 316 and the septum 360 define an open valve. As the tip 316 is spaced away from the passageway 364, and the upper surface 329b of the barrel 329 is spaced away from the base 360a of the septum 360, the aperture(s) 338 is placed in fluid communication with the opened passageway 364 for fluid flow therethrough.

The plunger 325 is biased in the direction from the second or open position to the first or closed position to normally close the aperture(s) 338. In the illustrated embodiment, the second port 310 includes a coil spring 336 that biases the plunger 325 in the direction from the second or open position to the first or closed position. The spring 336 encircles both the first shaft 312a and the barrel 329, and is mounted between the base end of the first shell 326 and a laterally-extending projection 329f of the barrel 329. The barrel 329 and second shell 327 are dimensioned such that in the first position, the projection 329f abuts the internal surface of the lip 327e, and in the second position the projection 329f abuts a stop surface 312c of the first shaft 312a. As may be recognized by those of ordinary skill in the pertinent art based on the teachings herein, the plunger 325 may be biased in any of numerous different ways that are currently known or that later become known, using biasing members other than springs, and if a spring is used, any of numerous different springs or combinations of springs may be used, e.g., a dome-shaped spring.

As shown in FIGS. 13A and 13B, a syringe or other delivery device 370 mates with the second port 310 to aseptically or sterile transfer fluids between the device 370 and the storage chamber 320. In the illustrated embodiment, the delivery device 370 has a female Luer connector 371 at the distal end thereof, for mating with the male Luer connector 327c. The delivery device connector 371 defines an elongated hollow shaft 371a therein dimensioned to fit into the passageway 364 that engages the elongated tip 316 of the plunger 325 and, in turn, displaces the tip 316 and plunger 352, against the bias of the spring, from the first position to the second position during connection of the delivery device 370 to the connector 327c. Similar to the embodiments described above, the septum 360 may wipe the shaft 371a of the delivery device 370, of contaminants thereon during engagement and passage through the septum passageway 364 by the shaft 371a, to prevent the shaft from introducing such contaminants into the sterile interior of the sealed second port 310.

When the syringe 370 is fully connected to the connector 327c and thus the plunger 325 is in the second position (FIG. 13B), fluid can flow between the delivery device 370 and the storage chamber 320. In the case of the illustrated LUER connector, the male connector portion is threaded into the female connector portion, the resulting relative axial movement of the delivery device, specifically the shaft 371a, relative to the device 300, depresses or retracts the plunger 352 and thereby the tip 316 out of the passageway. It should be noted that the length of the passageway is less than the length of the shaft 371a so that upon full engagement of the delivery device 370 and device 300, the tip 316 is fully retracted out of the passageway, so as to define a fluid pathway between the delivery device 370 and the device 330 via the shaft hollow 371a, the passageway 364, the interior of the mid portion 327b, and the aperture(s) 338. For example, the delivery device 370 can dispense fluid through the hollow shaft 371c thereof, through the fluid-flow aperture(s) 338 and the barrel 329, through the first shaft 312a and, in turn, into the storage chamber 320. Conversely, the pouch 318 may be hung, such that when the plunger 325 is displaced into the second position by a delivery device 370, fluid may flow out of the storage chamber 320, through the first shaft 312a, the barrel 329 and out the fluid-flow aperture(s) 338, and, in turn, through the shaft 371a and into the device 370.

After the desired volume of fluid is transferred between the device 300 and the delivery device 370, the delivery device is disconnected (e.g., unthreaded) from the connector 327c. As the shaft 371a is withdrawn from the septum passageway 364, the spring 336 biases the plunger 325 and the tip 316 back into sealing engagement with the septum 360, to, in turn, maintain the sterility of the interior of the device 300.

In FIGS. 14A through 14F, another device is indicated generally by the reference numeral 400. The device 400 is substantially similar to the device 100 described above in connection with FIGS. 7-11, and therefore like reference numerals preceded by the numerals "4" or "5" are used to indicate like elements.

Like the female connector 110 of the device 100, the female connector 410 of the device 400 comprises a female shell 526 that houses a shaft 412. The shaft 412 receives the flexible valve member 416, the valve body 414, and the septum 460 therein, in a manner similar to that explained above with respect to the female connector 110 of the device 100 of FIGS. 7-11. As indicated above, the spring in the connectors of the present invention may take any of numerous different configurations. Accordingly, the spring 436 of the flexible valve member 416 is a coil spring. As also shown, the septum 460 of the valve body 414 includes a frangible portion 461 that covers the septum passageway 464. In addition, a diameter or width of the septum passageway 464 is such that, after piercing, the frangible portion 461 (or a portion thereof) can be positioned between the septum 460 and the tip 476 of the filling member 490 without impeding movement of the tip 476 through the septum passageway 464. A diameter or width of the axially-extending socket 432 is such that the socket 432 exerts a radial or compressive force on the tip 476 of the filling member to facilitate the wiping effect on the filling member 490.

The coil spring 436 of the flexible valve member 416 is mounted within the female shell 526, and more specifically, within the shaft 412 of the female shell 526. The coil spring 436 extends axially between the upper portion 424 of the flexible valve member 416 and a distal end of the female shell 526. The coil spring 436 can be manually compressed and maintained in a compressed state. Otherwise, the coil spring 436 naturally rebounds from a compressed state and naturally biases the flexible valve member 416 in a direction from an open position, where the sealing surface 428 of the flexible valve member 416 is out of engagement with the valve seat 456, into the normally closed position, where the sealing surface 428 sealingly engages the valve seat 456. In the illustrated embodiment, the coil spring 436 is cylindrical; however, as may be recognized by those of ordinary skill in the pertinent art based on the teachings herein, the coil spring 436 may alternatively have a non-cylindrical shape. In the illustrated embodiment, the coil spring 436 is made of a flexible metallic material; however, as may be recognized by those of ordinary skill in the pertinent art based on the teachings herein, the coil spring 436 may alternatively be formed of any of numerous different materials (e.g., plastic materials), that are currently known, or that later become known, for performing the function of the coil spring 436 as described herein.

The frangible portion 461 of the septum 460 covers and protects the septum passageway 464, until the frangible portion 461 is pierced by the filling member 490 during engagement of the male connector 470 and the female connector 410, as described further below. The frangible portion 461 is integrally formed with the septum 460 and defines a surface contiguous with the stop surface 462 of the septum 462. When pierced, the frangible portion 461 remains connected to the septum 462. The frangible portion 461 has a thickness that permits it be pierced by the filling member 490 during manual interconnection of the male and female connectors 470, 410. If desired, the frangible portion 461 may include one or more weakened areas (e.g., areas of reduced thickness) that define break or fracture locations of the frangible portion 461 to facilitate piercing and penetration thereof by the filling member 490.

The septum 460 is configured such that an upper area of the septum passageway 464 (i.e., proximate the stop surface 462 of the septum 460) defines a diameter or width that is larger than that of a lower area of the septum passageway 464 (i.e., proximate the flexible valve member 416). The septum 460 defines a septum shoulder 463 at the junction between the upper and lower areas of the septum passageway 464. The septum 460 is dimensioned such that the frangible portion 461, when pierced, may extend into the upper area of the septum passageway 464 (i.e., positioned between the tip 476 and the septum 460), but will not extend into the lower area of the passageway 464.

The socket 432 defines a diameter or width that is less than a diameter or width of the upper area of the septum passageway 464, and less than or equal to the diameter or width of the lower area of the septum passageway 464. The diameter or width of the socket 432 is such that the socket 432 exerts a radial or compressive force on the tip 476 during movement of the tip 476 therethrough in order to enhance the wiping of the tip 476, as described further below.

As shown in FIGS. 14A through 14F, the male connector 470 and the female connector 410 are connectable for the aseptic transfer of fluid therethrough in a manner similar to that explained above with respect to the device 100 of FIGS. 7-11. The male connector 470 and female connector 410 are engaged, as shown typically in FIG. 14B. As shown typically in FIG. 14C, the male connector 470 is pressed further into engagement with the female connector 410, and the tip 476 of the filling member 490 pierces and passes through the frangible portion 461 of the septum 460, into the septum passageway 464, and then into the socket 432. The socket 432 and, in the illustrated embodiment, the lower area of the septum passageway 464, exert a radial or compressive force on, and thereby wipe, the tip 476 of the filling member 490 and/or the shutter 484 of contaminants thereon during engagement and passage of the tip 476 therethrough. As show in FIG. 14D, as the male connector 470 is pressed into engagement with the female connector 410, the tip 476 of the filling member 490 engages a stop surface 433 located within the base of the socket 432. Then, as shown in FIG. 14E, as the male connector 470 is further pressed into engagement with the female connector 410, the tip 476 of the filling member 490 is pressed against the stop surface 433 of the socket 432. As shown in FIGS. 14D through 14F, this, in turn, depresses the flexible valve member 416 against the bias of the coil spring 436 from the closed position, where the valve seat 456 sealingly engages the sealing surface 428 of the flexible valve member 416, into the open position, where the sealing surface 428 is moved out of engagement with the valve seat 456. The closure 478 remains in place and compresses the coil spring element 486 of the male connector 470, to, in turn, move the ports 482 (see FIG. 14F) of the filling member 490 past the end of the shutter 484 into the second or open position. As the ports 482 are now past the septum 460, the septum 460 seals the ports 482 from the ambient atmosphere. In the open position of FIG. 14F, fluid may travel from a first fluid line (not shown), through the filling member 490, through the open ports 482 of the filling member 490, through the flow aperture(s) 458 extending between the sealing surface 428 of the flexible valve member 416 and the valve seat 456, through the coil spring 436 of the flexible valve member 416, into the shaft 412 of the female connector 410, and continuing to a second fluid line (not shown).

To disconnect the male and female connectors 470, 410, the connecting steps are generally reversed, as explained above with respect to the device 100 of FIGS. 7-11. During disconnection, the coil spring 436 of the flexible valve member 416 naturally rebounds to return the flexible valve member 416 from the open position, back into the normally closed position, where the sealing surface 428 thereof reengages the valve seat 456, and reseals the interior of the shaft 412 of the female connector 410 and any fluid therein from the ambient atmosphere.

As may be recognized by those of ordinary skill in the pertinent art based on the teachings herein, numerous changes and modifications may be made to the above-described and other embodiments of the present invention without departing from its scope as defined in the appended claims. For example, the components of the valve and filling device and/or the male and female connectors may be made of any of numerous different rigid or flexible materials that are currently known or that later become known for performing the functions of the various components. The valve and filling device may also be used with any of numerous different devices or containers, such as vials, syringes or other dispensers, or alternatively as part of a line, such as in a hospital environment for example. Further, the filing device and/or sealed empty device to be filled may be sterilized prior to filling with a fluid sterilant as disclosed in U.S. Provisional Patent Application No. 61/499,626, filed Jun. 21, 2011, entitled "Nitric Oxide Injection Sterilization Device and Method," which is hereby expressly incorporated by reference in its entirety as part of the present disclosure as if fully set forth herein. Also, the components of the female connectors described herein can additionally or alternatively include one or more of the wiping features described in U.S. patent application Ser. No. 14/214,890, filed Mar. 15, 2014, which is hereby expressly incorporated by reference in its entirety. Accordingly, this detailed description of embodiments is to be taken in an illustrative, as opposed to a limiting sense.

What is claimed is:

1. An apparatus comprising:
a device and a second device, wherein the device includes a tube including a first flow aperture, a second flow aperture in fluid communication with the first flow aperture, and a closure configured to hermetically seal the second flow aperture; the device adapted to be connected to the second device for fluid flow therebetween, wherein one or more of the closure or the tube is slidable relative to the other between (i) a first position where the closure hermetically seals the second flow aperture, and (ii) a second position where the closure and the tube are sufficiently slidably displaced relative to each other to open the second flow aperture, and wherein said one or more of the closure or the tube is biased in a direction from the second position toward the first position to normally close the second flow aperture and is configured such that, in the first position, the closure hermetically seals with respect to ambient atmosphere all surfaces of the device that a fluid can contact in the second position when connected with the second device, thereby allowing aseptic passage of fluid over said surfaces of the device; and
wherein the second device is connectable to the tube and includes a valve and a chamber, wherein the tube is connectable in fluid communication with the valve, and in the second position, the second flow aperture is connectable in fluid communication with an outlet of the valve to allow a flow of substance between the tube and the chamber; and
wherein the second device includes a septum overlying the valve, the tube includes a tip that is moveable through the septum, and the closure is engageable with the septum to allow movement of one or more of the tube or the closure relative to the other from the first position to the second position during or after said movement through the septum.

2. An apparatus as defined in claim 1, further including a spring biasing the closure in the direction from the second position toward the first position.

3. An apparatus as defined in claim 1, wherein one or more of the closure or the tube is movable from the second position toward the first position during or upon withdrawing the tube or closure from engagement with the second device.

4. An apparatus as defined in claim 1, wherein the closure extends annularly about the tube.

5. An apparatus as defined in claim 1, wherein the closure is engageable with a stop surface of the tube to stop the closure in the first position.

6. An apparatus as defined in claim 1, wherein a distal end of the closure is substantially flush with the tube.

7. An apparatus as defined in claim 1, wherein the tube defines a blunt tip.

8. An apparatus as defined in claim 7, wherein the tip is substantially curvilinear.

9. An apparatus as defined in claim 1, wherein the second flow aperture includes first and second apertures.

10. An apparatus as defined in claim 9, wherein the first and second apertures are located on substantially opposite sides of the tube relative to each other.

11. An apparatus as defined in claim 9, wherein the first and second apertures are located proximally adjacent a blunt tip of the tube, and the closure in the first position is substantially flush therewith.

12. An apparatus as defined in claim 11, wherein the closure includes a distal end engageable with a stop surface of the tube in the first position, and the device further includes a spring for biasing the closure in the direction from the second position toward the first position.

13. An apparatus as defined in claim 12, further comprising a plunger within the closure and extending about the tube, wherein the spring extends between a distal end of the plunger and the distal end of the closure.

14. An apparatus as defined in claim 12, wherein the closure is slidably mounted on the tube, the closure engages the stop surface and seals the second flow aperture with respect to ambient atmosphere in the first position, and one or more of the closure or the tube slides relative to the other to move from the first position to the second position and open the second flow aperture.

15. An apparatus as defined in claim 14, wherein the spring is one or more of a coil spring, an elastic spring or a bellows spring.

16. An apparatus as defined in claim 1, wherein the valve includes a recess, the-tip is receivable within the recess, and the closure is engageable with the septum to allow movement of one or more of the tube or the closure relative to the other from the first position to the second position during or after movement of the tube tip into the recess.

17. An apparatus as defined in claim 1, wherein the valve includes a tube-engaging surface movable between closed and open positions, and in the closed position the closure is in the first position, and in the open position, the closure is in the second position and the second flow aperture is in fluid communication with the outlet of the valve to allow substance to flow therethrough.

18. An apparatus as defined in claim 17, wherein the valve includes a spring that normally biases the valve in the direction from the open position to the closed position.

19. An apparatus as defined in claim 18, wherein the valve spring is elastic.

20. An apparatus as defined in claim 1, wherein the second device is configured to, when connected to the device, receive at least a portion of the device exposed to the ambient atmosphere when the device is not connected to the second device and thereby prevent said fluid from contacting said at least a portion of the device in the second position when connected with the second device.

21. An apparatus as defined in claim 1, wherein the valve includes a recess, the tip is receivable within the recess when the device is connected with the second device, and the recess sealingly engages any portion of the tip that has been exposed to ambient atmosphere so as to prevent any contact of said portion of the tip with fluid flowing between the device and the second device to maintain aseptic transfer fluid between the device and the second device.

22. An apparatus as defined in claim 1, wherein the septum is configured to wipe contaminants from at least a portion of the tube during movement of the tip through the septum.

23. An apparatus as defined in claim 1, wherein, during at least a portion of the movement of the tip through the septum, the closure is interposed between the second flow aperture and the septum to substantially prevent contact between the second flow aperture and the septum.

24. An apparatus comprising:
a device and a second device, wherein the device is adapted to be connected to the second device and comprises: first means for the flow of substance therethrough; second means in fluid communication with the first means for the passage of the substance from the first means therethrough; third means for opening and hermetically sealing the second means, wherein the third means and first means are slidable relative to the other such that one or more of the first means or the third means is movable between (i) a first position where the third means hermetically seals the second means, and (ii) a second position where the first means and the third means are sufficiently slidably displaced relative to the other to open the second means; and fourth means for engaging the second device;
the second device comprising fifth means overlying a sixth means for engaging the fourth means prior to the fourth means engaging the sixth means when the device and second device are in a connected positions with each other;
wherein the third means are configured such that, in the first position, the third means hermetically seals with respect to ambient atmosphere all surfaces of the first and second means that a fluid can contact in the second position when connected with the second device, thereby allowing aseptic passage of the fluid over said surfaces of the first and second means; and
wherein the third means is engageable with the fifth means for allowing movement of one or more of the first means or the third means relative to each other from a closed position to a open position during or after said movement through the fifth means.

25. An apparatus as defined in claim 24, wherein the first means is a tube, the second means is a flow aperture of the tube, the third means is a closure, the fourth means is a tip, the fifth means is a septum, the sixth means is a valve.

26. An apparatus as defined in claim 24, wherein the second means includes seventh means for passage of fluid through the second means.

27. A method comprising the following steps:
transferring an aseptic or sterile substance between a cannula and a second device, the cannula including a tube that includes a first flow aperture, a second flow aperture in fluid communication with the first flow aperture, a tip and a closure configured to hermetically seal the second flow aperture, wherein one or more of the closure or the tube is slidable relative to the other between (i) a first position where the closure hermetically seals the second flow aperture, and (ii) a second position where the closure and tube are sufficiently slidably displaced relative to the other to open the second flow aperture;
sealing the second flow aperture of the cannula with respect to ambient atmosphere and preventing the flow of aseptic or sterile substance in the cannula from flowing through the second flow aperture;
engaging the tip with a second device, the second device comprising a chamber, a valve, and a septum overlying the valve;
moving the tip through the septum;
engaging the closure with the septum; and
opening the second flow aperture of the cannula and transferring the aseptic or sterile substance through the second flow aperture and through the valve, wherein the closure is configured such that, in the first position, the closure hermetically seals with respect to ambient atmosphere all surfaces of the tube the aseptic or sterile substance can contact in the second position, and allowing movement of one or more of the tube or the closure relative to the other from the first position to the second position during or after said movement of the tip through the septum.

28. A method as defined in claim 27, further comprising placing the second flow aperture of the cannula in fluid communication with the chamber of the second device prior to opening the second flow aperture.

29. A method as defined in claim 27, wherein the step of opening further comprises moving one or more of the closure or the tube between (i) the first position, and (ii) the second position.

30. A method as defined in claim 27, wherein the engaging step further comprises opening the valve to allow the transfer of substance through the valve.

31. A method as defined in claim 30, wherein the step of opening the valve comprises moving a flexible valve member of the valve from a sealingly closed position to an open position.

32. A method as defined in claim 31, further comprising disengaging the cannula from the valve; and before or during the disengaging step, moving one or more of the closure or the tube from the second position to the first position, and moving the valve from the open position to the sealingly closed position.

33. A method as defined in claim 32, wherein during the engaging and disengaging steps, substantially preventing any contact between the second flow aperture of the cannula and the septum.

34. A method as defined in claim 32, further comprising interposing the closure between the second flow aperture of the cannula and the septum to substantially prevent any contact between the second flow aperture and the septum.

35. A method as defined in claim 32, further comprising performing the engaging, transferring and disengaging steps in a non-sterile environment or an environment defining a SAL of about log 3 or less; transferring the substance between the cannula and into the chamber; and maintaining the sterility of the substance throughout the engaging, transferring and disengaging steps.

36. A method as defined in claim 27, further comprising maintaining the chamber substantially sealed with respect to ambient atmosphere during the step of transferring the aseptic or sterile substance through the valve.

37. A method as defined in claim 27, further including wiping contaminants from at least a portion of the tube during movement of the tip through the septum.

38. An apparatus comprising: a device and a second device, the device including a tube including a first flow aperture, a second flow aperture in fluid communication with the first flow aperture, and a closure movably mounted on the tube configured to hermetically seal the second flow aperture; the device adapted to be connected to the second device for fluid flow therebetween, wherein one or more of the closure or the tube moves relative to the other between (i) a first position where the closure hermetically seals the second flow aperture, and (ii) a second position where the closure and the tube are sufficiently displaced relative to each other to open the second flow aperture, and wherein the closure is configured such that, in the first position, the closure hermetically seals with respect to ambient atmosphere all surfaces of the device that a fluid can contact in the second position when connected with the second device, thereby allowing aseptic passage of fluid over said surfaces of the device; and
- wherein the second device is connectable to the tube and includes a valve and a chamber, wherein the tube is connectable in fluid communication with the valve, and in the second position, the second flow aperture is connectable in fluid communication with an outlet of the valve to allow a flow of substance between the tube and the chamber; and
- wherein the second device includes a septum overlying the valve, the tube includes a tip that is moveable through the septum, and the closure is engageable with the septum to allow movement of one or more of the tube or the closure relative to the other from the first position to the second position during or after said movement through the septum.

39. An apparatus as defined in claim 38, further including a spring biasing the closure in the direction from the second position toward the first position.

40. An apparatus as defined in claim 39, wherein the spring is one or more of a coil spring, an elastic spring or a bellows spring.

41. An apparatus as defined in claim 38, wherein one or more of the closure or the tube slides from the second position toward the first position during or upon withdrawing the tube or closure from engagement with the second device.

42. An apparatus as defined in claim 38, wherein the closure is engageable with a stop surface of the tube to stop the closure in the first position.

43. An apparatus as defined in claim 38, wherein a distal end of the closure is substantially flush with the tube.

44. An apparatus as defined in claim 38, wherein the valve includes a recess, the tip is receivable within the recess, and the closure is engageable with the septum to allow movement of one or more of the tube or the closure relative to the other from the first position to the second position during or after movement of the tube tip into the recess.

45. An apparatus as defined in claim 44, wherein the valve includes a spring that normally biases the valve in the direction from the open position to the closed position.

46. An apparatus as defined in claim 38, wherein the valve includes a recess, the tip is receivable within the recess when the device is connected with the second device, and the recess sealingly engages any portion of the tip that has been exposed to ambient atmosphere so as to prevent any contact of said portion of the tip with fluid flowing between the device and the second device to maintain aseptic transfer fluid between the device and the second device.

47. An apparatus as defined in claim 38, wherein the septum is configured to wipe contaminants from at least a portion of the tube during movement of the tip through the septum.

48. An apparatus as defined in claim 38, wherein during at least a portion of the movement of the tip through the septum, the closure is interposed between the second flow aperture and the septum to substantially prevent contact between the second flow aperture and the septum.

49. A device comprising:
- a tube including a first flow aperture, a second flow aperture in fluid communication with the first flow aperture, a closure configured to hermetically seal the second flow aperture, a plunger within the closure and extending about the tube, and a spring extending between a distal end of the plunger and a distal end of the closure;
- wherein the device is adapted to be connected to a second device for fluid flow therebetween, wherein one or more of the closure or the tube is movable relative to the other between (i) a first position where the closure hermetically seals the second flow aperture, and (ii) a second position where the closure and the tube are sufficiently displaced relative to each other to open the second flow aperture, and
- is configured such that, in the first position, the closure hermetically seals with respect to ambient atmosphere all surfaces of the device that fluid can contact in the second position when connected with the second device, thereby allowing aseptic passage of fluid over said surfaces of the device.

50. A device as defined in claim 49, wherein the closure is engageable with a stop surface of the tube to stop the closure in the first position.

51. A device as defined in claim 49, wherein a distal end of the closure is substantially flush with the tube.

* * * * *